United States Patent
Page et al.

(10) Patent No.: US 8,618,355 B2
(45) Date of Patent: Dec. 31, 2013

(54) AROMATIC PRENYLTRANSFERASE FROM HOP

(75) Inventors: Jonathan Page, Saskatoon (CA); Enwu Liu, Saskatoon (CA); Jana Nagel, Halle (DE)

(73) Assignee: National Research Council of Canada, Ottawa (CA)

( * ) Notice: Subject to any disclaimer, the term of this patent is extended or adjusted under 35 U.S.C. 154(b) by 398 days.

(21) Appl. No.: 12/922,905

(22) PCT Filed: Mar. 16, 2009

(86) PCT No.: PCT/CA2009/000336
§ 371 (c)(1),
(2), (4) Date: Sep. 16, 2010

(87) PCT Pub. No.: WO2009/114939
PCT Pub. Date: Sep. 24, 2009

(65) Prior Publication Data
US 2011/0021610 A1 Jan. 27, 2011

Related U.S. Application Data

(60) Provisional application No. 61/069,666, filed on Mar. 17, 2008.

(51) Int. Cl.
C12N 15/82 (2006.01)
C12N 15/74 (2006.01)
C07H 21/04 (2006.01)
C07K 14/415 (2006.01)

(52) U.S. Cl.
USPC ........ 800/278; 435/320.1; 435/471; 435/488; 530/370; 536/23.6; 800/285

(58) Field of Classification Search
None
See application file for complete search history.

(56) References Cited

U.S. PATENT DOCUMENTS

| | | | |
|---|---|---|---|
| 5,773,265 A | 6/1998 | Koike et al. | |
| 5,773,273 A | 6/1998 | Nishino et al. | |
| 5,776,911 A | 7/1998 | Szabo | |
| 5,786,192 A | 7/1998 | Obata et al. | |
| 5,786,193 A | 7/1998 | Greene et al. | |
| 5,789,558 A | 8/1998 | Casey et al. | |
| 5,807,725 A | 9/1998 | Ohto et al. | |
| 5,876,964 A | 3/1999 | Croteau et al. | |
| 5,882,909 A | 3/1999 | Ohto et al. | |
| 5,885,810 A | 3/1999 | Ohto et al. | |
| 5,912,154 A | 6/1999 | Ferro-Novick et al. | |
| 5,928,924 A | 7/1999 | Greene et al. | |
| 5,935,832 A | 8/1999 | Nakane et al. | |
| 6,020,177 A | 2/2000 | Koike et al. | |
| 6,040,165 A | 3/2000 | Narita et al. | |
| 6,043,072 A | 3/2000 | Croteau et al. | |
| 6,107,072 A | 8/2000 | Ishida | |
| 6,168,951 B1 | 1/2001 | Cahoon et al. | |
| 6,174,715 B1 | 1/2001 | Muramatsu et al. | |
| 6,225,096 B1 | 5/2001 | Narita et al. | |
| 6,225,097 B1 | 5/2001 | Obata et al. | |
| 6,265,633 B1 | 7/2001 | Okada et al. | |
| 6,287,810 B1 | 9/2001 | Huang et al. | |
| 6,303,330 B1 | 10/2001 | Croteau et al. | |
| 6,312,954 B1 | 11/2001 | Cahoon | |
| 6,316,216 B1 | 11/2001 | Ohto et al. | |
| 6,395,525 B2 | 5/2002 | Ohto et al. | |
| 6,410,280 B1 | 6/2002 | Obata et al. | |
| 6,410,827 B1 | 6/2002 | Cahoon et al. | |
| 6,413,761 B2 | 7/2002 | Obata et al. | |
| 6,639,127 B2 | 10/2003 | Okada et al. | |
| 6,645,747 B1 | 11/2003 | Hallahan et al. | |
| 6,855,868 B2 | 2/2005 | Cahoon et al. | |
| 6,933,374 B2 | 8/2005 | Okada et al. | |
| 7,060,815 B2 | 6/2006 | Okada et al. | |
| 7,091,019 B2 | 8/2006 | Okada et al. | |
| 7,109,391 B2 | 9/2006 | Cahoon et al. | |
| 7,199,283 B2 | 4/2007 | Cahoon et al. | |
| 7,205,456 B2 | 4/2007 | Hallahan et al. | |
| 7,217,862 B2 | 5/2007 | Cahoon et al. | |
| 7,273,737 B2 | 9/2007 | Hallahan et al. | |
| 7,348,469 B2 | 3/2008 | Cahoon et al. | |
| 7,361,483 B2 | 4/2008 | Kuzuyama et al. | |
| 7,390,643 B2 | 6/2008 | Croteau et al. | |
| 2002/0010952 A1 | 1/2002 | Okada et al. | |
| 2002/0106772 A1 | 8/2002 | Croteau et al. | |

(Continued)

FOREIGN PATENT DOCUMENTS

| | | |
|---|---|---|
| JP | 2005-137287 | 6/2005 |
| JP | 2006-280297 | 10/2006 |
| WO | WO 00/05382 | 7/1999 |
| WO | WO 2007/029577 | 8/2006 |

OTHER PUBLICATIONS

Sasaki et al, 2008, Plant Phys.,146:1075-1084.*
Colgate EC et al.; (2006) Xanthohumol, a prenylflavonoid derived from hops induces apoptosis and inhibits NF-kappaB activation in prostate . . . Cancer Lett 246: 201-209.
Collakova E et al. (2001) Isolation and functional analysis of homogentisate phytyltransferase from *Synechocystis* sp. PCC 6803 and *Arabidopsis*. Plant Physiol 127: 1113-1124.
Goto K et al; (2005) Enhanced antitumor activity of xanthohumol, a diacylglycerol acyltransferase inhibitor, under hypoxia. Cancer Lett 219: 215-222.

(Continued)

Primary Examiner — Anne Grunberg
Assistant Examiner — Jason Deveau Rosen
(74) Attorney, Agent, or Firm — Dahna S. Pasternak; Pasternak Patent Law

(57) ABSTRACT

Nucleic acid molecules from hop (*Humulus lupulus*) have been isolated and characterized wherein said nucleic acid molecules encode polypeptides having aromatic prenyltransferase activity Expression or over-expression of said nucleic acid molecules alters the level of terpenophenolic compounds The polypeptides may be used in vivo or in vitro to produce terpenophenolic compounds (e g, prenylated acylphloroglucmols and prenylflavonoids) such as prenyl-PIVP, prenyl-PIBP, humulone, lupulone, desmethylxanthohumol and xanthohumol.

12 Claims, 11 Drawing Sheets

(56) References Cited

U.S. PATENT DOCUMENTS

| | | |
|---|---|---|
| 2004/0137567 A1 | 7/2004 | Matsuda et al. |
| 2004/0191271 A1 | 9/2004 | Fennell et al. |
| 2005/0208639 A1 | 9/2005 | Ammirati et al. |
| 2005/0221459 A1 | 10/2005 | Taylor et al. |
| 2007/0020743 A1 | 1/2007 | Concha et al. |
| 2007/0067866 A1 | 3/2007 | Fukusaki et al. |
| 2007/0162993 A1 | 7/2007 | Cahoon et al. |
| 2007/0169217 A1 | 7/2007 | Cahoon et al. |
| 2007/0199099 A1 | 8/2007 | Hallahan et al. |
| 2008/0096276 A1 | 4/2008 | Hallahan et al. |
| 2008/0139449 A1 | 6/2008 | Jahnke et al. |
| 2012/0110703 A1 | 5/2012 | Yazaki et al. |

OTHER PUBLICATIONS

Jennewein S et al. (2004) Cytochrome p450 taxadiene 5alpha-hydroxylase, a mechanistically unusual monooxygenase catalyzing the first oxygenation step . . . Chem Biol 11: 379-387.

Lamy V et al.;(2007) Chemopreventive effects of lupulone, a hop {beta}-acid, on human colon cancer-derived metastatic SW620 cells and in a rat . . . Carcinogenesis 28: 1575-1581.

Lee JC et al.; (2007) Humulone inhibits phorbol ester-induced COX-2 expression in mouse skin by blocking activation of NF-kappaB and AP-1 . . . Carcinogenesis 28: 1491-1498.

Matousek J et al.; (2002) Cloning and characterisation of chs-specific DNA and cDNA sequences from hop (*Humulus lupulus* L.). Plant Science 162: 1007-1018.

Milligan SR et al. (2000) The endocrine activities of 8-prenylnaringenin and related hop (*Humulus lupulus* L.) . . . Journal of Clinical Endocrinology and Metabolism 85: 4912-4915.

Nagel J et al.; (2008) EST analysis of hop glandular trichomes identifies an O-methyltransferase that catalyzes the biosynthesis of xanthohumol. Plant Cell 20: 186-200.

Page JE, Nagel J (2006) Biosynthesis of terpenophenolics in hop and cannabis. In JT Romeo, ed, Integrative Plant Biochemistry, vol. 40. Elsevier, Oxford, pp. 179-210.

Paniego NB et al.; (1999) Phlorisovalerophenone synthase, a novel polyketide synthase from hop (*Humulus lupulus* L.) cones. European Journal of Biochemistry 262: 612-616.

Sasaki K et al.; (2008) Cloning and Characterization of Naringenin 8-Prenyltransferase, a Flavonoid-Specific Prenyltransferase of Sophora . . . Plant Physiol 146: 1075-1084.

Shimamura M et al.; (2001) Inhibition of angiogenesis by humulone, a bitter acid from beer hop. Biochem Biophys Res Commun 289: 220-224.

Siragusa GR et al.; (2008) Antimicrobial activity of lupulone against *Clostridium perfringens* in the . . . J Antimicrob Chemother PMID: 18276602 Feb. 18, 2008 [Epub ahead of print].

Stevens JF, Page JE (2004) Xanthohumol and related prenylflavonoids from hops and beer: to your good health! Phytochemistry 65: 1317-1330.

Verzele M (1986) Centenary review 100 Years of hop chemistry and its relevance to brewing. J. Inst. Brew. 92: 32-48.

Yajima H et al.; (2004) Isohumulones, bitter acids derived from hops, activate both peroxisome proliferator-activated receptor . . . J Biol Chem 279: 33456-33462.

Yazaki K et al. (2002) Geranyl diphosphate:4-hydroxybenzoate geranyltransferase from *Lithospermum erythrorhizon*. Cloning and characterization of . . . J Biol Chem 277: 6240-6246.

Zanoli P, Zavatti M (2008) Pharmacognostic and pharmacological profile of *Humulus lupulus* L. J Ethnopharmacol Jan. 20, 2008 [Epub ahead of print].

Zuurbier KWM et al.; (1998) In vitro prenylation of aromatic intermediates in the biosynthesis of bitter acids in *Humulus lupulus*. Phytochemistry 49: 2315-2322.

Dursina, B. et al.; (2006) Indentification and specificity profiling of protein prenyltransferase . . . Journal of the American Chemical Society.vol. 128(9) pp. 2822-2835.

ISR-Written-Opinion-on-PCT-CA2009-000336 dated Jun. 30, 2009.

\* cited by examiner

Xanthohumol

Desmethylxanthohumol

Xanthogalenol

4'-O-Methylxanthohumol

5'-Prenylxanthohumol

Xanthohumol B

Xanthohumol C

Xanthohumol D

8-Prenylnaringenin

Isoxanthohumol

A.

B.

C.

AROMATIC PRENYLTRANSFERASE FROM HOP

CROSS-REFERENCE TO RELATED APPLICATIONS

This application is a national entry of International Patent Application PCT/CA2009/000336 filed Mar. 16, 2009 and claims the benefit of U.S. Provisional Patent Application USSN 61/069,666 filed Mar. 17, 2008, the entire contents of both of which are herein incorporated by reference.

FIELD OF THE INVENTION

The present invention relates to aromatic prenyltransferase enzyme from hop, a nucleotide sequence encoding the enzyme and uses of the nucleotide sequence for altering terpenophenolic production in organisms.

BACKGROUND OF THE INVENTION

Hops, the cones of the female hop plant (*Humulus lupulus* L.), are a key ingredient in beer and responsible for the bitter taste of this widely consumed beverage. Compounds from hops also have biological activities that may make them useful as pharmaceuticals or nutraceuticals, or leads for the development of pharmaceutical drugs (Zanoli and Zavatti, 2008). Although hop contains a wide range of phytochemicals, including polyphenols, stilbenes, essential oils (monoterpenes and sesquiterpenes) (Verzele, 1986), it is the terpenophenolics that are the most important for beer brewing and also have potential as medicinal agents (Verzele, 1986). Terpenophenolics may also be called prenylated polyketides. The terpenophenolics in hop can be divided into the prenylated acylphloroglucinols (most commonly called bitter acids) and the prenylflavonoids. The prenylated acylphloroglucinols include the alpha-acids (humulone, cohumulone and related compounds) and the beta-acids (lupulone, colupulone and related compounds) (FIG. 1). The alpha-acids isomerize during the brewing process giving rise to the bitter isohumulones. Several biological activities have been attributed to the humulones (Shimamura et al., 2001; Yajima et al., 2004; Lee et al., 2007) and lupulones (Lamy et al., 2007; Siragusa et al., 2008).

The main prenylflavonoid in hop is xanthohumol but related compounds such as desmethylxanthohumol, xanthogalenol and isoxanthohumol are also present (FIG. 2). Xanthohumol possesses a range of biological activities, which include antioxidation, cytoprotection via phase 2 protein induction and anticancer activities (reviewed in Stevens and Page, 2004; Goto et al., 2005; Colgate et al., 2006). The immediate metabolic precursor of xanthohumol, desmethylxanthohumol, isomerizes during brewing to form 6-prenylnaringenin and 8-prenylnaringenin. 8-Prenylnaringenin is the most potent phytoestrogen thus far identified (Milligan et al., 2000).

The biosynthetic pathways leading to the terpenophenolics in hop follow a common catalytic pattern consisting of three phases: polyketide formation through the action of a polyketide synthase, aromatic prenylation and cyclization/decoration (Page and Nagel, 2006). The proposed biosynthetic pathways leading to the major bitter acids and xanthohumol are shown in FIGS. 3 and 4, respectively.

The type III polyketide synthase responsible for the formation of the acylphloroglucinol core of the bitter acids compounds has been identified. Paniego et al. purified and cloned valerophenone synthase (VPS) (also called phlorisovalerophenone synthase) from hop (Paniego et al., 1999) (FIG. 3). The enzyme uses isovaleryl CoA or isobutyryl CoA as primers for polyketide formation. VPS gave phlorisovalerophenone (PIVP), which is the precursor for humulone and lupulone, when supplied with isovaleryl CoA and malonyl CoA. Similarly, VPS catalyzed the condensation of isobutyryl CoA and malonyl CoA to yield phlorisobutyrophenone (PIBP), the precursor for cohumulone and colupulone. The second phase of bitter acid biosynthesis involves prenylation of PIVP and PIBP. Prenylation of PIVP with one dimethylallyl diphosphate (DMAPP) molecule yields prenyl-PIVP and a second prenylation gives diprenyl-PIVP (also called deoxyhumulone). Prenylation of PIVP with three DMAPP molecules yields lupulone. The aromatic prenyltransferase(s) that carry out these reactions have not been identified. Zuurbier and co-workers showed that protein extracts from hop cones were capable of forming prenyl-PIVP, prenyl-PIBP, deoxyhumulone and deoxycohumulone from DMAPP and PIVP or PIBP (Zuurbier et al., 1998). The oxidase that converts deoxyhumulone to humulone has also not been identified at the gene or protein level.

The first step in prenylflavonoid biosynthesis is the condensation of p-coumaroyl CoA with three molecules of malonyl CoA to give chalconaringenin (also called naringenin chalcone), a reaction catalyzed by the type III polyketide synthase enzyme chalcone synthase (FIG. 4). Aromatic prenylation of the A ring of chalconaringenin with DMAPP yields desmethylxanthohumol, which is subsequently methylated at the 6'-hydroxyl group to form xanthohumol. Our group has recently identified the O-methyltransferase enzyme that performs this reaction (Nagel et al., 2008).

As discussed, only three genes encoding enzymes in hop terpenophenolic biosynthesis are known: i) valerophenone synthase, which catalyzes the formation of the polyketide moiety of bitter acid biosynthesis (Paniego et al., 1999), ii) chalcone synthase which forms the polyketide moiety of xanthohumol (Matousek et al, 2002) and iii) desmethylxanthohumol O-methyltransferase, which methylates desmethylxanthohumol to yield xanthohumol (Nagel et al., 2008). The aromatic prenyltransferase(s) participating in both of these pathways are not known.

As noted above, the genes encoding aromatic prenyltransferase enzyme(s) participating in either the bitter acid or prenylflavonoids pathways are unknown. However, several aromatic prenyltransferases involved in other branches of plant metabolism have been identified. These include a prenyltransferase that geranylates hydroxybenzoic acid in the shikonin biosynthetic pathway (Yazaki et al., 2002), a homogentisic acid prenyltransferase from *Arabidopsis* (Collakova and DellaPenna, 2001) and a recently discovered flavonoid prenyltransferase from *Sophora flavescens* (Sasaki et al., 2008).

Hop terpenophenolics are valuable plant-derived natural products. Enhanced production of bitter acids, xanthohumol or other hop terpenophenolics such as desmethylxanthohumol could be achieved though breeding and selection programs as well as genetic engineering with the use of genes encoding enzymes of the terpenophenolic biosynthetic pathways. In addition, the biosynthetic pathways leading to these metabolites may be transferred to bacteria, yeast, fungi or other prokaryotic or eukaryotic organisms to engineer terpenophenolic production in these hosts. Enhancing terpenophenolic levels in hop plants, engineering their synthesis in other plants or transferring their biosynthesis to microorganisms such as yeast are possible routes to producing greater quantities of these metabolites for use by the brewing industry, as pharmaceuticals or for other purposes. In order for the metabolic engineering of hop terpenophenolics to be achieved, genes encoding the enzymes of terpenophenolic biosynthesis must be identified.

There remains a need in the art to identify aromatic prenyltransferase enzymes, and nucleotide sequences encoding such enzymes, that catalyze the transfer of prenyl groups.

SUMMARY OF THE INVENTION

In a first aspect of the invention, there is provided an isolated or purified nucleic acid molecule comprising a nucleotide sequence having at least 85% sequence identity to SEQ ID NO: 1 or 5.

In a second aspect of the invention, there is provided an isolated or purified polypeptide comprising an amino acid sequence having at least 85% sequence identity to SEQ ID NO: 2 or 6.

In a third aspect of the invention, there is provided a process of transferring a prenyl group comprising: reacting a prenyl group acceptor molecule with a prenyl group donor molecule in presence of an aromatic prenyltransferase of the present invention, thereby transferring the prenyl group from the prenyl group donor molecule to the prenyl group acceptor molecule.

In a fourth aspect of the invention, there is provided a method of altering levels of terpenophenolic compounds in an organism, cell or tissue comprising expressing or over-expressing a nucleic acid molecule of the present invention in the organism, cell or tissue.

In a fifth aspect of the present invention, there is provided a method of altering levels of terpenophenolic compounds in an organism, cell or tissue comprising using a nucleic acid molecule of the present invention, or a part thereof, to silence an aromatic prenyltransferase gene in the organism, cell or tissue.

Aromatic prenyltransferase enzymes, and nucleotide sequences encoding such enzymes, have now been identified and characterized. The nucleotide sequence may be used to create, through breeding, selection or genetic engineering, hop plants that overproduce terpenophenolic compounds of either the prenylated phloroglucinol or prenylflavonoid classes, for example xanthohumol, humulone, cohumulone, lupulone, colupulone or mixtures thereof. This prenyltransferase nucleotide sequence may also be used, alone or in combination with genes encoding other steps in the bitter acid and xanthohumol pathways, to engineer hop terpenophenolic biosynthesis in other plants or in microorganisms. In addition, knocking out this gene in hops could be used to block terpenophenolic biosynthesis and thereby reduce production of bitter acids and prenylflavonoids. The aromatic prenyltransferase may also be useful as a biocatalytic tool for prenylation of small molecules.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

Figure 1:
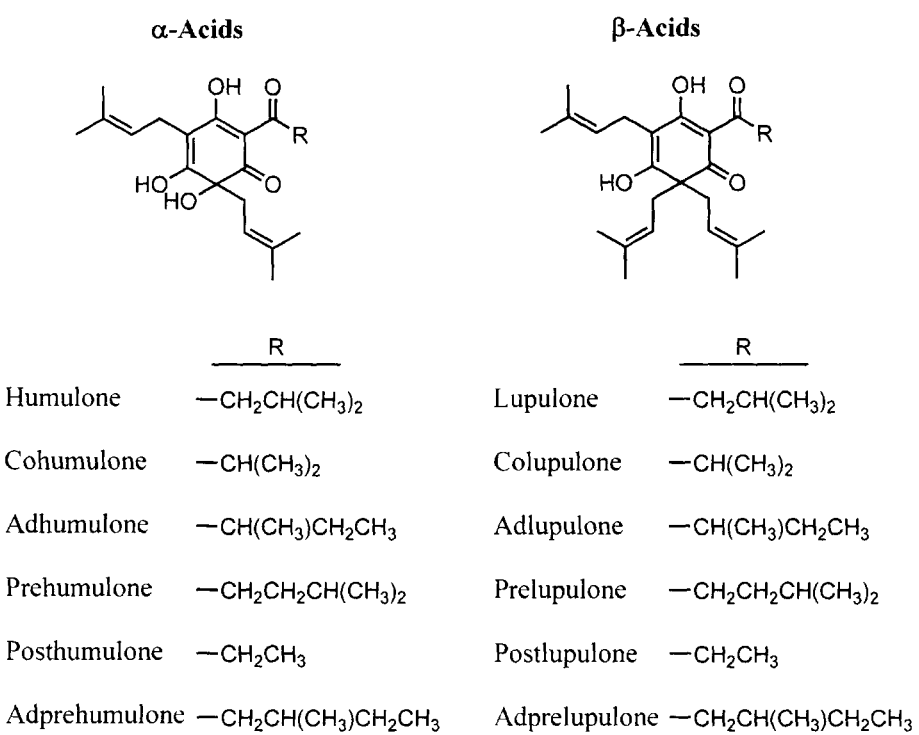
FIG. 1 depicts the structures of prenylated acylphloroglucinol derivatives (bitter acids) from hop.
Figure 2:
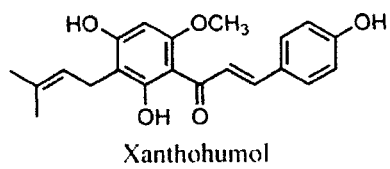
FIG. 2 depicts the structures of prenylflavonoids from hop.
Figure 2:
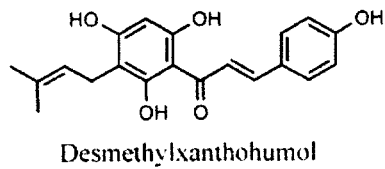
Figure 2:
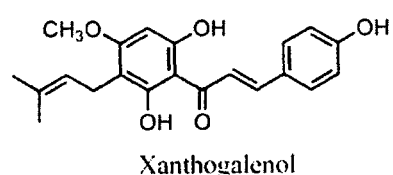
Figure 2:
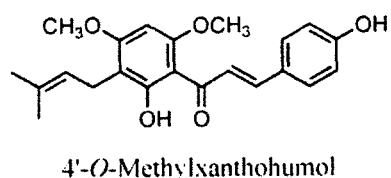
Figure 2:
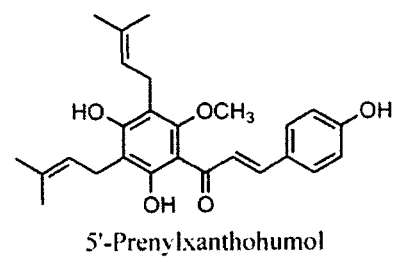
Figure 2:
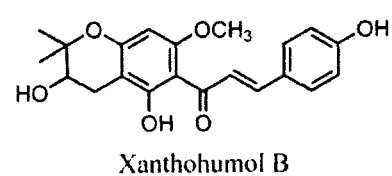
Figure 2:
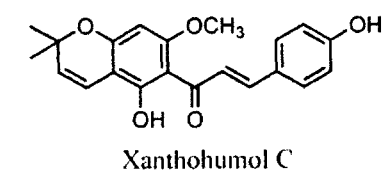
Figure 2:
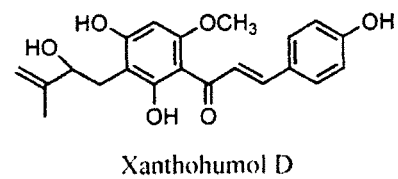
Figure 2:
Figure 2:
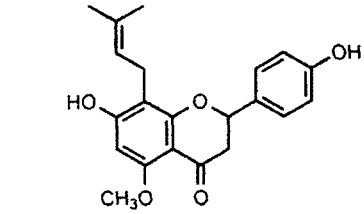
Figure 3:
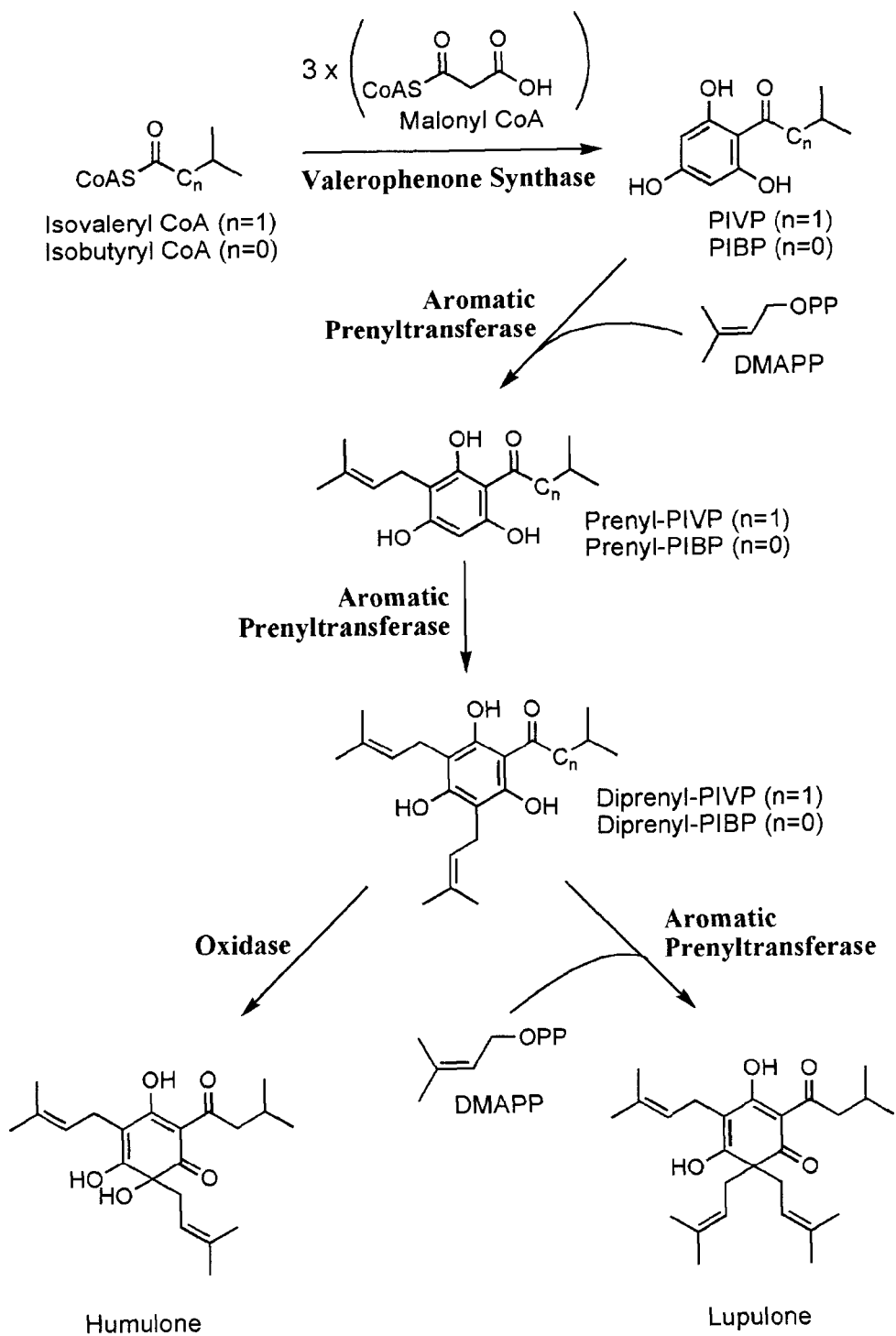
FIG. 3 depicts the biosynthetic pathway of the main prenylated acylphloroglucinol derivatives (bitter acids) in hop.
Figure 4:
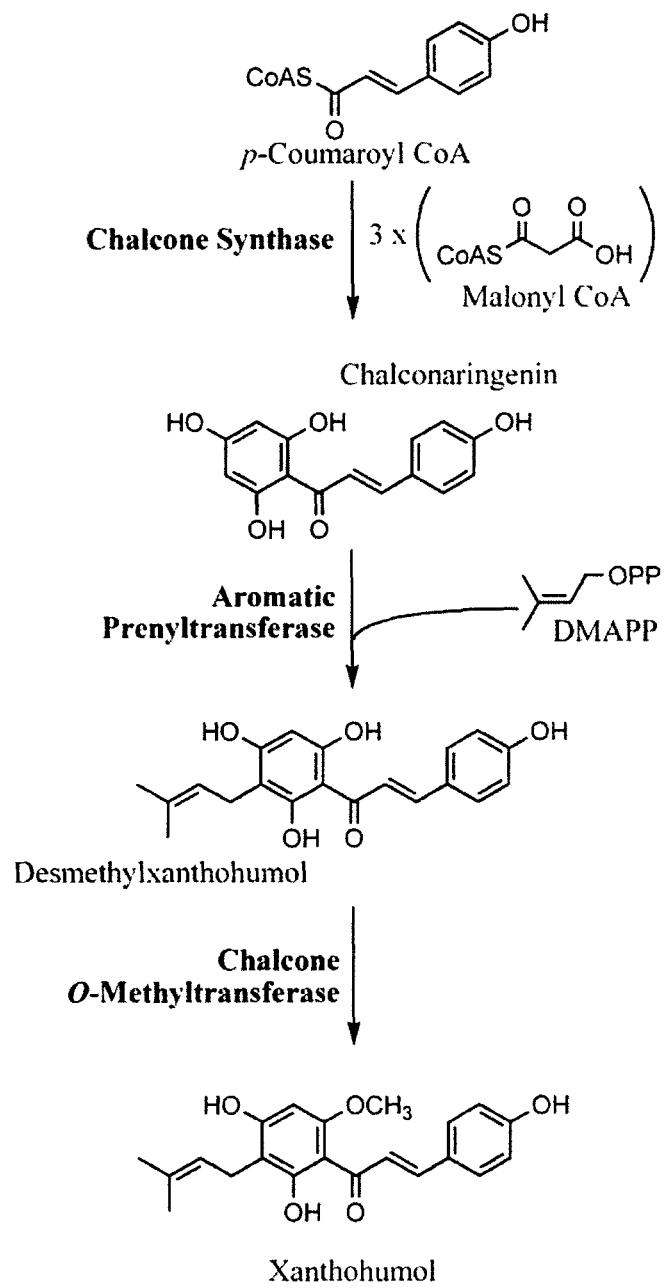
FIG. 4 depicts the biosynthetic pathway for the production of xanthohumol in hop.

Some embodiments of the present invention relate to an isolated or purified nucleic acid molecule having at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to SEQ ID NO: 1 or 5.

Further included are nucleic acid molecules that hybridize to the above disclosed sequences. Hybridization conditions may be stringent in that hybridization will occur if there is at least a 90%, 95% or 97% sequence identity with the nucleic acid molecule that encodes the enzyme of the present invention. The stringent conditions may include those used for known Southern hybridizations such as, for example, incubation overnight at 42° C. in a solution having 50% formamide, 5×SSC (150 mM NaCl, 15 mM trisodium citrate), 50 mM sodium phosphate (pH 7.6), 5×Denhardt's solution, 10% dextran sulfate, and 20 micrograms/milliliter denatured, sheared salmon sperm DNA, following by washing the hybridization support in 0.1×SSC at about 65° C. Other known hybridization conditions are well known and are described in Sambrook et al., Molecular Cloning: A Laboratory Manual, Third Edition, Cold Spring Harbor, N.Y. (2001).

As will be appreciated by the skilled practitioner, slight changes in nucleic acid sequence do not necessarily alter the amino acid sequence of the encoded polypeptide. It will be appreciated by persons skilled in the art that changes in the identities of nucleotides in a specific gene sequence that change the amino acid sequence of the encoded polypeptide may result in reduced or enhanced effectiveness of the genes and that, in some applications (e.g., anti-sense, co suppression, or RNAi), partial sequences often work as effectively as full length versions. The ways in which the nucleotide sequence can be varied or shortened are well known to persons skilled in the art, as are ways of testing the effectiveness of the altered genes. In certain embodiments, effectiveness may easily be tested by, for example, conventional gas chromatography. All such variations of the genes are therefore included as part of the present disclosure.

As will be appreciated by one of skill in the art, the length of the nucleic acid molecule described above will depend on the intended use. For example, if the intended use is as a primer or probe for example for PCR amplification or for screening a library, the length of the nucleic acid molecule will be less than the full length sequence, for example, 15-50 nucleotides. In these embodiments, the primers or probes may be substantially identical to a highly conserved region of the nucleic acid sequence or may be substantially identical to either the 5' or 3' end of the DNA sequence. In some cases, these primers or probes may use universal bases in some positions so as to be 'substantially identical' but still provide flexibility in sequence recognition. It is of note that suitable primer and probe hybridization conditions are well known in the art.

Some embodiments relate to an isolated or purified polypeptide having at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to the amino acid sequence as set forth in SEQ ID NO: 2 or 6.

Some embodiments relate to a vector, construct or expression system containing an isolated or purified polynucleotide having at least 85% sequence identity to SEQ ID NO: 1 or 5. Accordingly, there is provided a method for preparing a vector, construct or expression system including such a sequence, or a part thereof, for introduction of the sequence or partial sequence in a sense or anti-sense orientation, or a complement thereof, into a cell.

In some embodiments, the isolated and/or purified nucleic acid molecules, or vectors, constructs or expression systems comprising these isolated and/or purified nucleic acid molecules, may be used to create transgenic organisms or cells of organisms that produce polypeptides with aromatic prenyltransferase activity. Therefore, one embodiment relates to transgenic organisms, cells or germ tissues of the organism including an isolated and/or purified nucleic acid molecule having at least 85% sequence identity to SEQ ID NO: 1 or 5.

Preferably, the organism is a plant, microorganism or insect. Plants are preferably of the genus *Humulus* (hop), for example *Humulus japonicus*, *Humulus lupulus* (e.g. *Humulus lupulus* subsp. *lupulus*, *Humulus lupulus* subsp. *cordifolius*, *Humulus lupulus* subsp. *lupuloides*, *Humulus lupulus* subsp. *neomexicanus* and *Humulus lupulus* subsp. *pubescens*) and *Humulus yunnanensis*. Microorganisms are preferably bacteria (e.g. *Escherichia coli*) or yeast (e.g. *Saccharomyces cerevisiae*). Insect is preferably *Spodoptera frugiperda*.

Organisms, cells and germ tissues of this embodiment may have altered levels of terpenophenolic compounds. With reference to FIGS. 1-4, it will be appreciated by one skilled in the art that expression or over-expression of the nucleic acid molecule will result in expression or over-expression of the aromatic prenyltransferase enzyme which may result in increased production of terpenophenolic compounds such as desmethylxanthohumol, xanthohumol, mono-, di- and tri-prenylated derivatives of PIVP, mono-, di- and tri-prenylated derivatives of PIPB, humulone, lupulone, etc. Silencing of aromatic prenyltransferase in the organism, cell or tissue will result in under-expression of the aromatic prenyltransferase which may result in accumulation of precursors to the aforementioned compounds.

Expression or over-expression of the nucleic acid molecule may be done in combination with expression or over-expression of one or more other nucleic acids that encode one or more enzymes in a terpenophenolic biosynthetic pathway. Some examples of other nucleic acids include: nucleic acids that encode a valerophenone synthase that catalyzes the formation of the polyketide moiety of bitter acid biosynthesis (Paniego et al., 1999); nucleic acids that encode chalcone synthase which forms the polyketide moiety of xanthohumol (Matousek et al, 2002); nucleic acids that encode a deoxyhumulone oxidase that converts deoxyhumulones to humulones (Fung et al, 1997); and, desmethylxanthohumol O-methyltransferase that methylates desmethylxanthohumol to yield xanthohumol (Nagel et al., 2008).

Expression or over-expression of the aromatic prenyltransferase enzyme of the present invention compared to a control which has normal levels of the enzyme for the same variety grown under similar or identical conditions will result in increased levels of terpenophenolic compounds, for example, 1-20%, 2-20%, 5-20%, 10-20%, 15-20%, 1-15%, 1-10%, 2-15%, 2-10%, 5-15%, or 10-15% (w/w).

Transfer of a prenyl group from a prenyl group donor molecule to a prenyl group acceptor molecule in the presence of an aromatic prenyltransferase of the present invention may be accomplished in vivo or in vitro. As previously mentioned, such transfers in vivo may be accomplished by expressing or over-expressing the nucleic acid molecule in an organism, cell or tissue. The organism, cell or tissue may naturally contain the prenyl group acceptor molecule and/or the prenyl group donor molecule, or the prenyl group receptor molecule and/or prenyl group donor molecule may be provided to the organism, cell or tissue for uptake and subsequent reaction.

In vitro, the prenyl group acceptor molecule, prenyl group donor molecule and aromatic prenyltransferase may be mixed together in a suitable reaction vessel to effect the reaction. In vitro, the aromatic prenyltransferase may be used in combination with other enzymes to effect a complete synthesis of a target compound from a precursor. For example, such other enzymes may be implicated in a terpenophenolic biosynthetic pathway, e.g. valerophenone synthase that catalyzes the formation of the polyketide moiety of bitter acid biosynthesis, chalcone synthase which forms the polyketide moiety of xanthohumol, deoxyhumulone oxidase that converts deoxyhumulones to humulones and desmethylxanthohumol O-methyltransferase that methylates desmethylxanthohumol to yield xanthohumol.

Prenyl group acceptor molecules include any suitable molecule having an aromatic group to which a prenyl group may be transferred. For example, the aromatic prenyltransferase may catalyze all of the prenylation reactions in humulone, lupulone and xanthohumol biosynthesis. For example, acylphloroglucinol or flavonoid compounds (e.g. phlorisovalerophenone (PIVP), phlorisobutyryphenone (PIBP), prenyl-PIVP, prenyl-PIPB, diprenyl-PIVP, diprenyl-PIPB and chalconaringenin) may be prenyl group acceptor molecules. Prenyl group donor molecules include any suitable molecule containing a transferable prenyl group. The prenyl group donor molecule may be based on one or more prenyl moieties, for example dimethylallyldiphosphate (DMAPP) and geranyl diphosphate (GPP). The prenyl group donor molecule is preferably DMAPP. Prenyl groups are 3-methyl-2-buten-1-yl moieties.

Terms:

In order to facilitate review of the various embodiments of the disclosure, the following explanations of specific terms are provided:

Complementary nucleotide sequence: "Complementary nucleotide sequence" of a sequence is understood as meaning any nucleic acid molecule whose nucleotides are complementary to those of sequence of the disclosure, and whose orientation is reversed (antiparallel sequence).

Degree or percentage of sequence homology: The term "degree or percentage of sequence homology" refers to degree or percentage of sequence identity between two sequences after optimal alignment. Percentage of sequence identity (or degree or identity) is determined by comparing two optimally aligned sequences over a comparison window, where the portion of the peptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity.

Homologous isolated and/or purified sequence: "Homologous isolated and/or purified sequence" is understood to mean an isolated and/or purified sequence having a percentage identity with the bases of a nucleotide sequence, or the amino acids of a polypeptide sequence, of at least about 85%, 86%, 87%, 88%, 89%, 90%, 91%, 92%, 93%, 94%, 95%, 96%, 97%, 98%, 99%, 99.5%, 99.6%, or 99.7%. This percentage is purely statistical, and it is possible to distribute the differences between the two nucleotide sequences at random and over the whole of their length. Sequence identity can be determined, for example, by computer programs designed to perform single and multiple sequence alignments. It will be appreciated that this disclosure embraces the degeneracy of codon usage as would be understood by one of ordinary skill in the art. Furthermore, it will be understood by one skilled in the art that conservative substitutions may be made in the amino acid sequence of a polypeptide without disrupting the structure or function of the polypeptide. Conservative substitutions are accomplished by the skilled artisan by substituting amino acids with similar hydrophobicity, polarity, and R-chain length for one another. Additionally, by comparing aligned sequences of homologous proteins from different species, conservative substitutions may be identified by locating amino acid residues that have been mutated between species without altering the basic functions of the encoded proteins.

Increasing, decreasing, modulating, altering or the like: As will be appreciated by one of skill in the art, such terms refers to comparison to a similar variety grown under similar conditions but without the modification resulting in the increase, decrease, modulation or alteration. In some cases, this may be an untransformed control, a mock transformed control, or a vector-transformed control.

Isolated: As will be appreciated by one of skill in the art, "isolated" refers to polypeptides or nucleic acids that have been "isolated" from their native environment.

Nucleotide, polynucleotide, or nucleic acid sequence: "Nucleotide, polynucleotide, or nucleic acid sequence" will be understood as meaning both double-stranded or single-stranded in the monomeric and dimeric (so-called in tandem) forms and the transcription products thereof.

Sequence identity: Two amino-acids or nucleotidic sequences are said to be "identical" if the sequence of amino-acids or nucleotidic residues in the two sequences is the same when aligned for maximum correspondence as described below. Sequence comparisons between two (or more) peptides or polynucleotides are typically performed by comparing sequences of two optimally aligned sequences over a segment or "comparison window" to identify and compare local regions of sequence similarity. Optimal alignment of sequences for comparison may be conducted by the local homology algorithm of Smith and Waterman, Ad. App. Math 2: 482 (1981), by the homology alignment algorithm of Needleman and Wunsch, J. Mol. Biol. 48: 443 (1970), by the search for similarity method of Pearson and Lipman, Proc. Natl. Acad. Sci. (U.S.A.) 85: 2444 (1988), by computerized implementation of these algorithms (GAP, BESTFIT, FASTA, and TFASTA in the Wisconsin Genetics Software Package, Genetics Computer Group (GCG), 575 Science Dr., Madison, Wis.), or by visual inspection.

The definition of sequence identity given above is the definition that would be used by one of skill in the art. The definition by itself does not need the help of any algorithm, said algorithms being helpful only to achieve the optimal alignments of sequences, rather than the calculation of sequence identity.

From the definition given above, it follows that there is a well defined and only one value for the sequence identity between two compared sequences which value corresponds to the value obtained for the best or optimal alignment.

Stringent hybridization: Hybridization under conditions of stringency with a nucleotide sequence is understood as meaning a hybridization under conditions of temperature and ionic strength chosen in such a way that they allow the maintenance of the hybridization between two fragments of complementary nucleic acid molecules. Homologs of the HIPT1 genes described herein obtained from other organisms, for example plants, may be obtained by screening appropriate libraries that include the homologs, wherein the screening is performed with the nucleotide sequence of the specific HIPT1 genes disclosed herein, or portions or probes thereof, or identified by sequence homology search using sequence alignment search programs such as BLAST, FASTA.

Methods:

Nucleic acid isolation and cloning is well established. Similarly, an isolated gene may be inserted into a vector and transformed into a cell by conventional techniques. Nucleic acid molecules may be transformed into an organism. As known in the art, there are a number of ways by which genes, vectors, constructs and expression systems can be introduced into organisms, and a combination of transformation and tissue culture techniques have been successfully integrated into effective strategies for creating transgenic organisms. These methods, which can be used in the invention, have been described elsewhere (Potrykus, 1991; Vasil, 1994; Walden and Wingender, 1995; Songstad et al., 1995), and are well known to persons skilled in the art. Suitable vectors are well known to those skilled in the art and are described in general technical references such as Pouwels et al., (1986). Particularly suitable vectors include the Ti plasmid vectors. For example, one skilled in the art will certainly be aware that, in addition to *Agrobacterium* mediated transformation of *Arabidopsis* by vacuum infiltration (Bechtold, et al. 1993) or wound inoculation (Katavic et al., 1994), it is equally possible to transform other plant species, using *Agrobacterium* Ti-plasmid mediated transformation (e.g., hypocotyl (DeBlock et al., 1989) or cotyledonary petiole (Moloney et al., 1989) wound infection), particle bombardment/biolistic methods (Sanford et al., 1987; Nehra. et al., 1994; Becker et al., 1994) or polyethylene glycol-assisted, protoplast transformation (Rhodes et al., 1988; Shimamoto et al., 1989) methods.

As will also be apparent to persons skilled in the art, and as described elsewhere (Meyer, 1995; Datla et al., 1997), it is possible to utilize promoters to direct any intended up- or down-regulation of transgene expression using constitutive promoters (e.g., those based on CaMV35S), or by using promoters which can target gene expression to particular cells, tissues (e.g., napin promoter for expression of transgenes in developing seed cotyledons), organs (e.g., roots), to a particular developmental stage, or in response to a particular external stimulus (e.g., heat shock).

Promoters for use herein may be inducible, constitutive, or tissue-specific or have various combinations of such characteristics. Useful promoters include, but are not limited to constitutive promoters such as carnation etched ring virus (CERV), cauliflower mosaic virus (CaMV)35S promoter, or more particularly the double enhanced cauliflower mosaic virus promoter, comprising two CaMV 35S promoters in tandem (referred to as a "Double 35S" promoter). It may be desirable to use a tissue-specific or developmentally regulated promoter instead of a constitutive promoter in certain circumstances. A tissue-specific promoter allows for over-expression in certain tissues without affecting expression in other tissues.

The promoter and termination regulatory regions will be functional in the host cell and may be heterologous (that is, not naturally occurring) or homologous (derived from the plant host species) to the cell and the gene. Suitable promoters which may be used are described above.

The termination regulatory region may be derived from the 3' region of the gene from which the promoter was obtained or from another gene. Suitable termination regions which may be used are well known in the art and include *Agrobacterium tumefaciens* nopaline synthase terminator (Tnos), *A. tumefaciens* mannopine synthase terminator (Tmas) and the CaMV 35S terminator (T35S). Particularly preferred termination regions for use herein include the pea ribulose bisphosphate carboxylase small subunit termination region (TrbcS) or the Tnos termination region. Such gene constructs may suitably be screened for activity by transformation into a host plant via *Agrobacterium* and screening for altered terpenophenolic levels.

The nucleic acid molecule or fragments thereof may be used to block terpenophenolic biosynthesis in organisms that naturally produce terpenophenolic compounds. Silencing using a nucleic acid molecule of the present invention may be accomplished in a number of ways generally known in the art, for example, RNA interference (RNAi) techniques, artificial microRNA techniques, virus-induced gene silencing (VIGS) techniques, antisense techniques, sense co-suppression techniques and targeted mutagenesis techniques.

RNAi techniques involve stable transformation using RNA interference (RNAi) plasmid constructs (Helliwell and Waterhouse, 2005). Such plasmids are composed of a fragment of the target gene to be silenced in an inverted repeat structure. The inverted repeats are separated by a spacer, often an intron. The RNAi construct driven by a suitable promoter, for example, the Cauliflower mosaic virus (CaMV) 35S promoter, is integrated into the plant genome and subsequent transcription of the transgene leads to an RNA molecule that folds back on itself to form a double-stranded hairpin RNA. This double-stranded RNA structure is recognized by the plant and cut into small RNAs (about 21 nucleotides long) called small interfering RNAs (siRNAs). siRNAs associate with a protein complex (RISC) which goes on to direct degradation of the mRNA for the target gene.

Artificial microRNA (amiRNA) techniques exploit the microRNA (miRNA) pathway that functions to silence endogenous genes in plants and other eukaryotes (Schwab et al, 2006; Alvarez et al, 2006). In this method, 21 nucleotide long fragments of the gene to be silenced are introduced into a pre-miRNA gene to form a pre-amiRNA construct. The pre-miRNA construct is transferred into the organism genome using transformation methods apparent to one skilled in the art. After transcription of the pre-amiRNA, processing yields amiRNAs that target genes which share nucleotide identity with the 21 nucleotide amiRNA sequence.

In RNAi silencing techniques, two factors can influence the choice of length of the fragment. The shorter the fragment the less frequently effective silencing will be achieved, but very long hairpins increase the chance of recombination in bacterial host strains. The effectiveness of silencing also appears to be gene dependent and could reflect accessibility of target mRNA or the relative abundances of the target mRNA and the hpRNA in cells in which the gene is active. A fragment length of between 100 and 800 bp, preferably between 300 and 600 bp, is generally suitable to maximize the efficiency of silencing obtained. The other consideration is the part of the gene to be targeted. 5' UTR, coding region, and 3' UTR fragments can be used with equally good results. As the mechanism of silencing depends on sequence homology there is potential for cross-silencing of related mRNA sequences. Where this is not desirable a region with low sequence similarity to other sequences, such as a 5' or 3' UTR, should be chosen. The rule for avoiding cross-homology silencing appears to be to use sequences that do not have blocks of sequence identity of over 20 bases between the construct and the non-target gene sequences. Many of these same principles apply to selection of target regions for designing amiRNAs.

Virus-induced gene silencing (VIGS) techniques are a variation of RNAi techniques that exploits the endogenous antiviral defenses of plants. Infection of plants with recombinant VIGS viruses containing fragments of host DNA leads to post-transcriptional gene silencing for the target gene. In one embodiment, a tobacco rattle virus (TRV) based VIGS system can be used.

Antisense techniques involve introducing into a plant an antisense oligonucleotide that will bind to the messenger RNA (mRNA) produced by the gene of interest. The "antisense" oligonucleotide has a base sequence complementary to the gene's messenger RNA (mRNA), which is called the "sense" sequence. Activity of the sense segment of the mRNA is blocked by the anti-sense mRNA segment, thereby effectively inactivating gene expression. Application of antisense to gene silencing in plants is described in more detail by Stam et al., 2000.

Sense co-suppression techniques involve introducing a highly expressed sense transgene into a plant resulting in reduced expression of both the transgene and the endogenous gene (Depicker et al., 1997). The effect depends on sequence identity between transgene and endogenous gene.

Targeted mutagenesis techniques, for example TILLING (Targeting Induced Local Lesions IN Genomes) and "delete-a-gene" using fast-neutron bombardment, may be used to knockout gene function in an organism (Henikoff, et al., 2004; Li et al., 2001). TILLING involves treating germplasm or individual cells with a mutagen to cause point mutations that are then discovered in genes of interest using a sensitive method for single-nucleotide mutation detection. Detection of desired mutations (e.g. mutations resulting in the inactivation of the gene product of interest) may be accomplished, for example, by PCR methods. For example, oligonucleotide primers derived from the gene of interest may be prepared and PCR may be used to amplify regions of the gene of interest from organisms in the mutagenized population. Amplified mutant genes may be annealed to wild-type genes to find mismatches between the mutant genes and wild-type genes. Detected differences may be traced back to the organism which had the mutant gene thereby revealing which mutagenized organism will have the desired expression (e.g. silencing of the gene of interest). These organisms may then be selectively bred to produce a population having the desired expression. TILLING can provide an allelic series that includes missense and knockout mutations, which exhibit reduced expression of the targeted gene. TILLING is touted as a possible approach to gene knockout that does not involve introduction of transgenes, and therefore may be more acceptable to consumers. Fast-neutron bombardment induces mutations, i.e. deletions, in organism genomes that can also be detected using PCR in a manner similar to TILLING.

EXAMPLES

Example 1

Isolation and Characterization of HIPT1 Gene and Enzyme

Lupulin glands were purified from cones of the hop cultivars Taurus and Nugget. RNA was extracted and used to construct four lupulin-gland specific cDNA libraries. cDNA clones were selected at random and sequenced from the 5' end to obtain an EST dataset of 10,581 ESTs. The ESTs were compared to the NCBI non-redundant (nr) database using the BLASTX algorithm.

Seventeen ESTs in the EST dataset showed similarity to homogentisate phytyltransferase VTE2-2, a prenyltransferase that catalyzes the prenylation of homogentisic acid (HGA) with phytyldiphosphate in tocopherol biosynthesis (Collakova and DellaPenna, 2001). Based on the consensus sequence of the prenyltransferase-like cDNA, oligonucleotide primers (5'-CCTA GTCGACATGGAGCTCTCTTCAGTTTCTAGC-3' (SEQ ID NO: 3) with SalI site underlined and start codon in bold) and (5'-TAAC GCGGCCGCCTAAATGAACAGATATACAACG-3' (SEQ ID NO: 4) with NotI site underlined) were designed to amplify the open reading frame (ORF) of the prenlyltransferase gene. PCR was performed using first-strand cDNA synthesized from lupulin gland RNA as template, Pfu polymerase and an annealing temperature of 56° C. The purified PCR product was digested with SalI and NotI, cloned into a similarly digested pFastBacHTC vector (Invitrogen) and sequenced.

Two ORF's from *Humulus lupulus* HIPT1 cDNA were characterized (SEQ ID NO: 1 and SEQ ID NO: 5). One is 1239 nucleotides long while the other is shorter at 1227 nucleotides. The short ORF lacks a 12 by stretch of nucleotides and is probably a splice variant of the longer one. The extra 12 by stretch in the longer ORF is at nucleotides 161-172 of SEQ ID NO: 1. The two ORF nucleotide sequences are shown below with the amino acid sequences of the predicted proteins. Both the short and long ORF's encode functional aromatic prenyltransferases.

```
Humulus lupulus HIPT1: (SEQ ID NO: 1)
long ORF - 1239 nucleotides
ATGGAGCTCTCTTCAGTTTCTAGCTTTTCACTTGGAACTAATCCATTT
ATATCAATCCCCCATAATAATAATAATCTCAAGGTCTCATCTTACTGT
TGTAAAAGCAAGAGCAGAGTAATCAATTCCACAAACTCAAAGCATTGT
TCCCCCAACAACAACAGCAACAACAACACCTCTAACAAGACAACACAT
CTTCTTGGGTTGTACGGACAGAGCAGATGCTTATTAAAACCTTTATCA
TTTATCAGCTGCAACGACCAAAGGGGAAATTCAATTAGGGCTTCTGCA
CAAATTGAAGATCGACCTCCTGAATCTGGAAATCTTTCGGCACTTACA
AATGTTAAAGACTTTGTAAGTGTATGTTGGGAGTATGTAAGACCATAC
ACAGCAAAAGGAGTTATTATATGCTCTAGTTGTTTATTTGGAAGAGAA
TTGTTGGAGAACCCAAATCTATTTAGTTGGCCTCTAATTTTTAGGGCA
CTCTTGGGAATGTTGGCTATACTGGGCTCTTGTTTTTATACAGCTGGC
ATCAATCAAATTTTTGATATGGATATTGACAGGATAAACAAACCAGAT
TTACCACTGGTTTCAGGGCGTATTTCTGTGGAATCAGCTTGGTTATTG
ACGTTAAGTCCTGCAATAATTGGCTTCATATTGATTCTTAAATTGAAC
TCAGGACCACTCCTTACTTCTCTATACTGTTTGGCCATTTTGAGTGGG
ACTATCTATTCTGTTCCTCCATTTAGATGGAAGAAGAATCCCATTACA
GCATTTCTTTGTATTCTTATGATTCATGCAGGTTTAAACTTTTCTGTA
TATTATGCCTCTAGAGCAGCACTTGGACTTGCATTTGCATGGAGCCCT
TCATTTTCCTTCATCACTGCCTTTATTACATTTATGACGCTAACGTTG
GCTTCCTCCAAAGATCTTTCTGACATAAATGGAGATCGCAAGTTTGGT
GTTGAAACCTTTGCAACCAAGCTTGGTGCAAAAAACATTACATTACTT
GGCACAGGACTTCTCCTCCTAAACTATGTAGCAGCTATATCTACTGCC
ATTATATGGCCTAAGGCTTTCAAGAGTAACATAATGCTGCTTTCTCAT
GCAATCTTAGCATTTTCCTTAATCTTCCAGGCTCGAGAGTTGGATCGA
ACGAACTACACTCCGGAAGCGTGCAAAAGCTTCTATGAATTCATCTGG
ATCCTCTTCTCTGCGGAATACGTTGTATATCTGTTCATT Humulus lupulus HIPT1: (SEQ ID NO: 2)
enzyme encoded by the long ORF - 413 amino acids
MELSSVSSFSLGTNPFISIPHNNNNLKVSSYCCKSKSRVINSTNSKHC
SPNNNSNNNTSNKTTHLLGLYGQSRCLLKPLSFISCNDQRGNSIRASA
QIEDRPPESGNLSALTNVKDFVSVCWEYVRPYTAKGVIICSSCLFGRE
LLENPNLFSWPLIFRALLGMLAILGSCFYTAGINQIFDMDIDRINKPD
LPLVSGRISVESAWLLTLSPAIIGFILILKLNSGPLLTSLYCLAILSG
TIYSVPPFRWKKNPITAFLCILMIHAGLNFSVYYASRAALGLAFAWSP
SFSFITAFITFMTLTLASSKDLSDINGDRKFGVETFATKLGAKNITLL
GTGLLLLNYVAAISTAIIWPKAFKSNIMLLSHAILAFSLIFQARELDR
TNYTPEACKSFYEFIWILFSAEYVVYLFI Humulus lupulus HIPT1: (SEQ ID NO: 5)
short ORF - 1227 nucleotides
ATGGAGCTCTCTTCAGTTTCTAGCTTTTCACTTGGAACTAATCCATTT
ATATCAATCCCCCATAATAATAATAATCTCAAGGTCTCATCTTACTGT
TGTAAAAGCAAGAGCAGAGTAATCAATTCCACAAACTCAAAGCATTGT
TCCCCCAACAACAACACCTCTAACAAGACAACACATCTTCTTGGGTTG
TACGGACAGAGCAGATGCTTATTAAAaCCTTTATCAtTTATCAGCTGC
AACGACCAAAGGGGAAATTCAATTAGGGCTTCTGCACAAATTGAAGAT
CGACCTCCTGAATCTGGAAATCTTTCGGCACTTACAAATGTTAAAGAC
TTTGTAAGTGTATGTTGGGAGTATGTAAGACCATACACAGCAGAAAGGA
GTTATTATATGCTCTAGTTGTTTATTTGGAAGAGAATTGTTGGAGAAC
CCAAATCTATTTAGTTGGCCTCTAAtTTTTAGGGCACTCTTGGGAATG
TTGGCTATACTGGGCTCTTGTTTTTATACAGCTGGCATCAATCAAATT
TTTGATATGGATATTGACAGGATAAACAAACCAGATTTACCACTGGTT
TCAGGGCGTATTTCTGTGGAATCAGCTTGGTTATTGACGTTAAGTCCT
GCAATAATTGGCTTCATATTGATTCTTAAATTGAACTCAGGACCACTC
CTTACTTCTCTATACTGTTTGGCCATTTTGAGTGGGACTATCTATTCT
GTTCCTCCATTTAGATGGAAGAATCCCATTACAGCATTTCTTTGT
ATTCTTATGATTCATGCAGGTTTAAACTTTTCTGTATATTATGCCTCT
AGAGCAGCACTTGGACTTGCATTTGCATGGAGCCCTTCATTTTCCTTC
ATCACTGCCTTTATTACATTTATGACGCTAACGTTGGCTTCCTCCAAA
GATCTTTCTGACATAAATGGAGATCGCAAGTTTGGTGTTGAAACCTTT
GCAACCAAGCTTGGTGCAAAAAACATTACATTACTTGGCACAGGACTT
CTCCTCCTAAACTATGTAGCAGCTATATCTACTGCCATTATATGGCCT
AAGGCTTTCAAGAGTAACATAATGCTGCTTTCTCATGCAATCTTAGCA
TTTTCCTTAATCTTCCAGGCTCGAGAGTTGGATCGAACGAACTACACT
CCGGAAGCGTGCAAAAGCTTCTATGAATTCATCTGGATCCTCTTCTCT
GCGGAATACGTTGTATATCTGTTCATT Humulus lupulus HIPT1: (SEQ ID NO: 6)
enzyme encoded by the short ORF - 409 amino acids
MELSSVSSFSLGTNPFISIPHNNNNLKVSSYCCKSKSRVINSTNSKHC
SPNNNSNKTTHLLGLYGQSRCLLKPLSFISCNDQRGNSIRASAQIED
RPPESGNLSALTNVKDFVSVCWEYVRPYTAKGVIICSSCLFGRELLEN
PNLFSWPLIFRALLGMLAILGSCFYTAGINQIFDMDIDRINKPDLPLV
SGRISVESAWLLTLSPAIIGFILILKLNSGPLLTSLYCLAILSGTIYS
VPPFRWKKNPITAFLCILMIHAGLNFSVYYASRAALGLAFAWSPSFSF
ITAFITFMTLTLASSKDLSDINGDRKFGVETFATKLGAKNITLLGTGL
LLLNYVAAISTAIIWPKAFKSNIMLLSHAILAFSLIFQARELDRTNYT
PEACKSFYEFIWILFSAEYVVYLFI
```

Example 2

Transfection of Sf9 Cells with HIPT1 Gene

The open reading frame (ORF) of HIPT1 gene cloned into the baculovirus expression vector pFastBacHTC (Invitrogen) was transformed into competent DH10Bac cells and the resulting bacmid generated using the Bac-to-Bac system (Invitrogen). The bacmid was used to transfect *Spodoptera frugiperda* (Sf9) insect cells. After amplification of the baculovirus through several passages, insect cell cultures were infected, cultivated for three days and then centrifuged to separate cells from culture media. Cell pellets were lysed and microsomes prepared according to Jennewein et al (2004).

Example 3

Biochemical Activity of HIPT1 Enzyme

Figure 5:
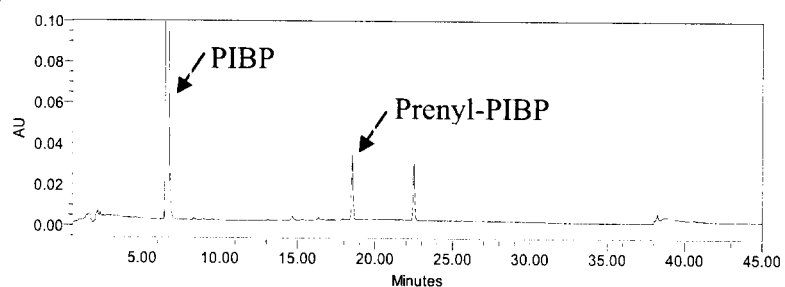
FIG. 5 depicts HPLC analysis of catalytic activity of HIPT1 with PIBP. (A) A complete enzyme assay (100 µl) containing 100 mM Tris-HCl pH 7.0, 10 mM $MgCl_2$, 0.5 mM PIBP, 0.5 mM dimethylallyldiphosphate (DMAPP) and 20 µl of microsomes from insect cells expressing recombinant HIPT1. (B) The same assay lacking microsomal proteins. (C) The same assay lacking DMAPP.
Figure 5:
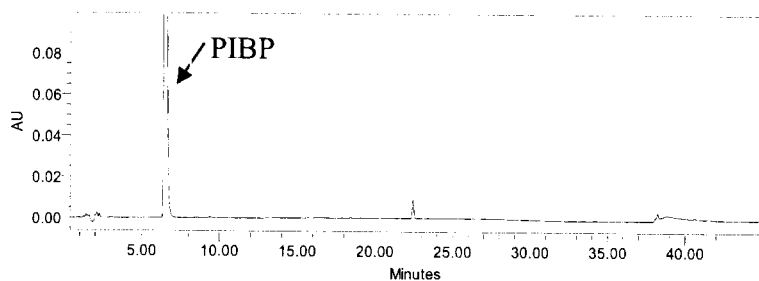
Figure 5:
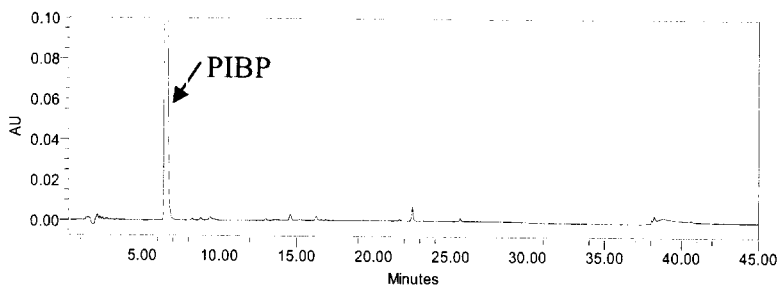
Figure 6:
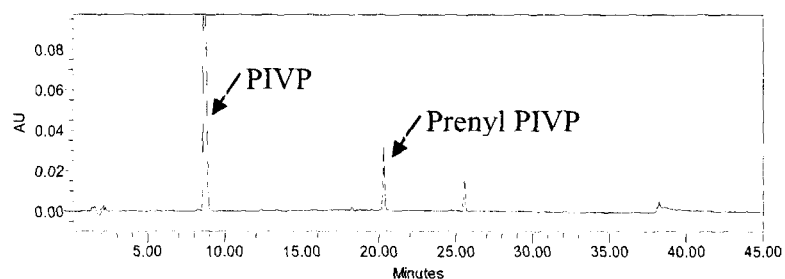
FIG. 6 depicts HPLC analysis of catalytic activity of HIPT1 with PIVP. (A) A complete enzyme assay (100 µl) containing 100 mM Tris-HCl pH 7.0, 10 mM $MgCl_2$, 0.5 mM PIVP, 0.5 mM dimethylallyldiphosphate (DMAPP) and 20 µl of microsomes from insect cells expressing recombinant HIPT1. (B) The same assay lacking microsomal proteins. (C) The same assay lacking DMAPP.
Figure 6:
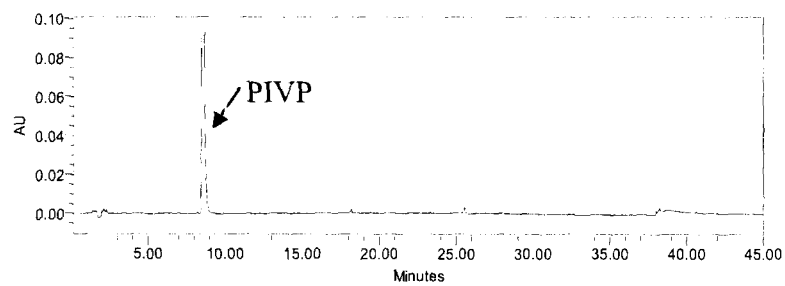
Figure 6:
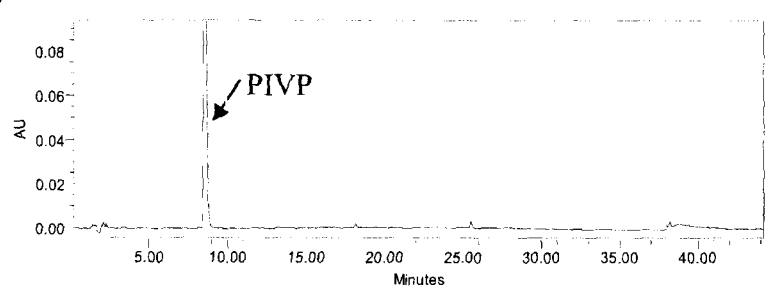
Figure 7:
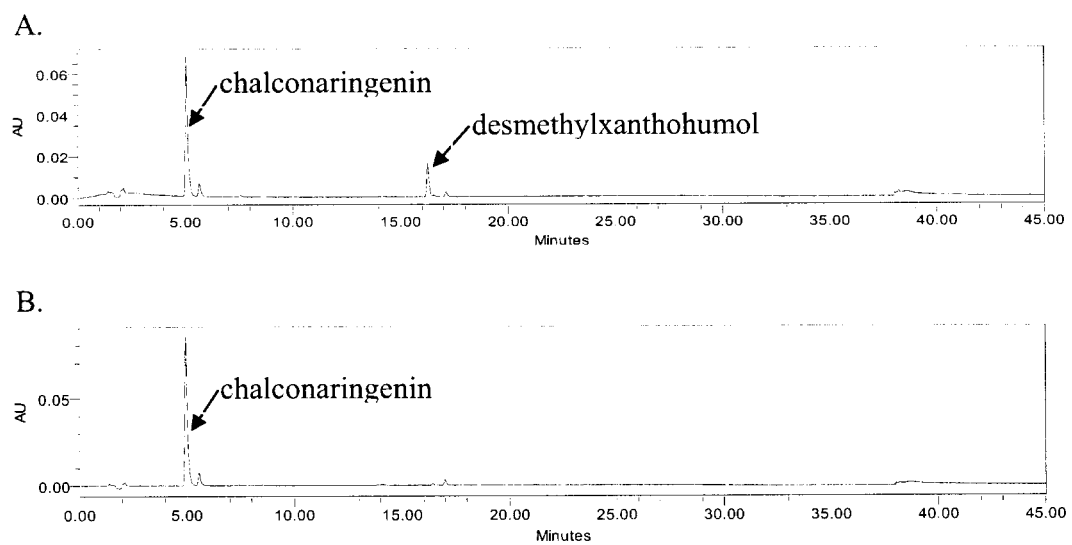
FIG. 7 depicts HPLC analysis of catalytic activity of HIPT1 with chalconaringenin. (A) A complete enzyme assay (100 µl) containing 100 mM Tris-HCl pH 7.0, 10 mM $MgCl_2$, 0.5 mM chalconaringenin, 0.5 mM dimethylallyldiphosphate (DMAPP) and 20 µl of microsomes from insect cells expressing recombinant HIPT1. (B) The same assay lacking DMAPP.

HIPT1 enzyme was assayed with phlorisobutyryphenone (PIBP), phlorisovalerophenone (PIVP) and chalconaringenin. Microsomal preparations from Example 2 were used in a 100 µl enzyme assay containing 100 mM Tris-HCl pH 7.0, 10 mM $MgCl_2$, 0.5 mM aromatic substrate (PIBP, PIVP or chalconaringenin), 0.5 mM dimethylallyldiphosphate (DMAPP) and 20 µl of microsomes from insect cells expressing recombinant HIPT1. The assays were incubated at 30° C. for 120 min, the reactions stopped by addition of 5 µl 6N HCl, the reaction products extracted with 200 µl ethyl acetate and dried. The dried products were resuspended in 100 µl of methanol and analyzed by reversed-phase HPLC (solvent A: 0.1% TFA in water, solvent B: acetonitrile; 0-10 min, 40% B to 50% B; 10-20 min, 50% B to 100% B; flow rate 1 ml/min). Product identification was confirmed by comparison with authentic standards and LC-MS. The HIPT1 enzyme was found to catalyze the transfer of the C5 prenyl group of DMAPP to PIBP forming prenyl PIBP (FIG. 5), to PIVP forming prenyl PIVP (FIG. 6) and chalconaringenin forming desmethylxanthohumol (FIG. 7).

Figure 8:
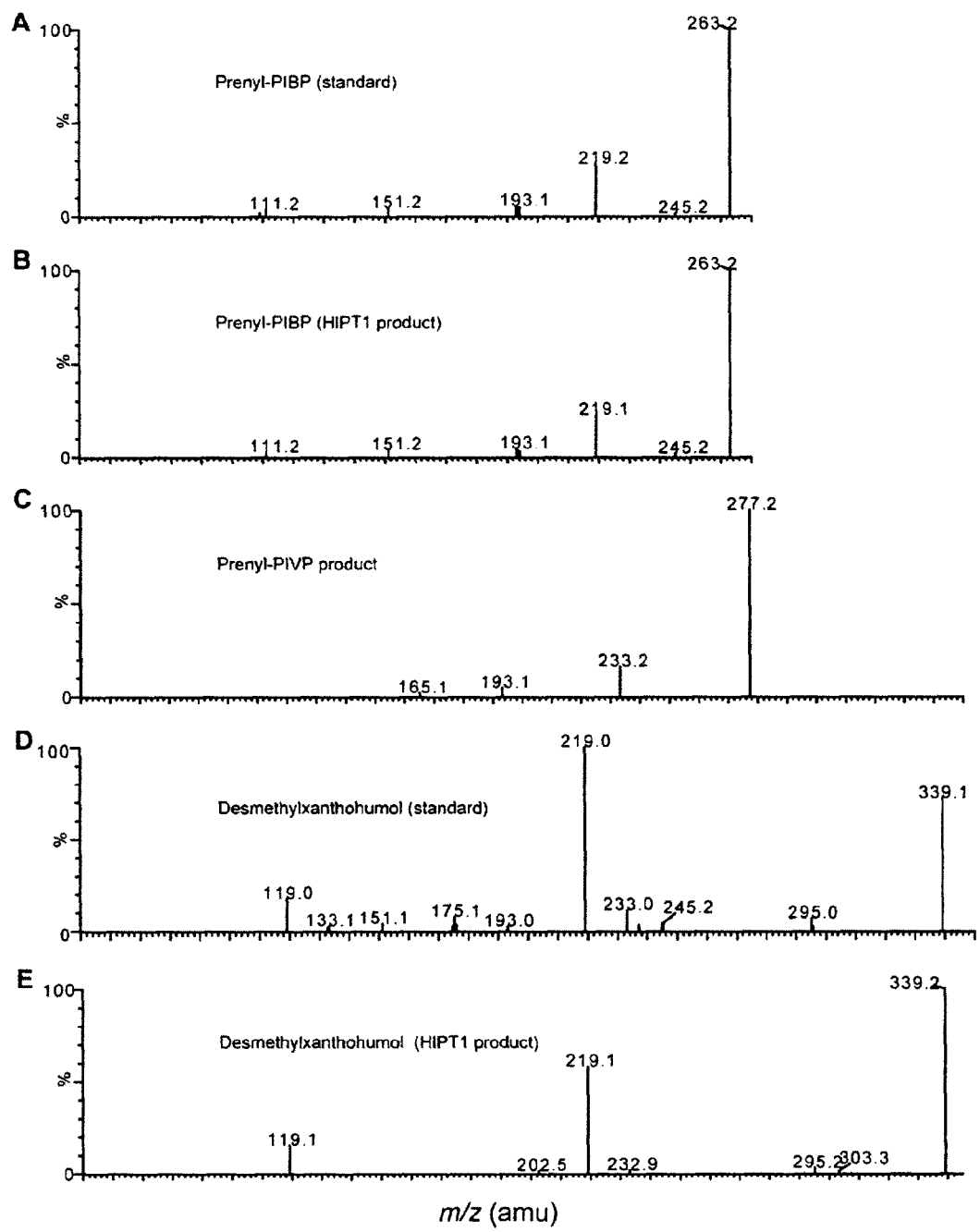
FIG. 8 depicts negative ion ESI-LC-MS LC-MS analysis of authentic standards and prenylated reaction products catalyzed by HIPT1 prenyltransferase.

FIG. 8 shows negative ion ESI-LC-MS spectra of authentic standards and prenylated reaction products catalyzed by HIPT1 prenyltransferase. FIG. 8A shows the mass spectrum of authentic prenyl-PIBP standard ((M-H)⁻ m/z 263). FIG. 8B shows the mass spectrum of reaction product obtained by prenylation of PIBP in the presence of DMAPP and HIPT1. Its mass, (M-H)⁻ m/z 263, and spectrum corresponds to that of prenyl-PIBP. The mass spectrum of reaction product obtained by prenylation of PIVP in the presence of DMAPP and HIPT1 is shown in FIG. 8C. No standard was available for prenyl-PIVP, however the mass of the reaction product peak corresponds to the calculated mass of prenyl-PIVP ((M-H)⁻ m/z 277). FIG. 8D shows the mass spectrum of authentic desmethylxanthumol standard ((M-H)⁻ m/z 339). FIG. 8E shows the mass spectrum of reaction product obtained by prenylation of chalconaringenin in the presence of DMAPP and HIPT1. Its mass, (M-H)⁻ m/z 339, and spectrum corresponds to that of desmethylxanthohumol. Abbreviations: PIBP is phlorisobutyrophenone, PIVP is phlorisovalerophenone, DMAPP is dimethylallyl diphosphate.

An enzyme kinetic analysis was performed and the rate constants ($K_m$) for the prenylation of various substrates catalyzed by HIPT1 are shown in Table 1.

TABLE 1

Kinetic properties of HIPT1

| Substrate | $K_m$ Substrate[b] (µM) |
|---|---|
| PIVP | 4.95 ± 0.25 |
| PIBP | 10.19 ± 0.55 |
| Chalconaringenin | 195.5 ± 24.8 |
| DMAPP | 16.78 ± 2.35[a] |

[a] Determined with PIVP as acceptor substrate
[b] Mean ± SD (n = 3)

Example 4

Substrate Specificity of HIPT1

Figure 9A:
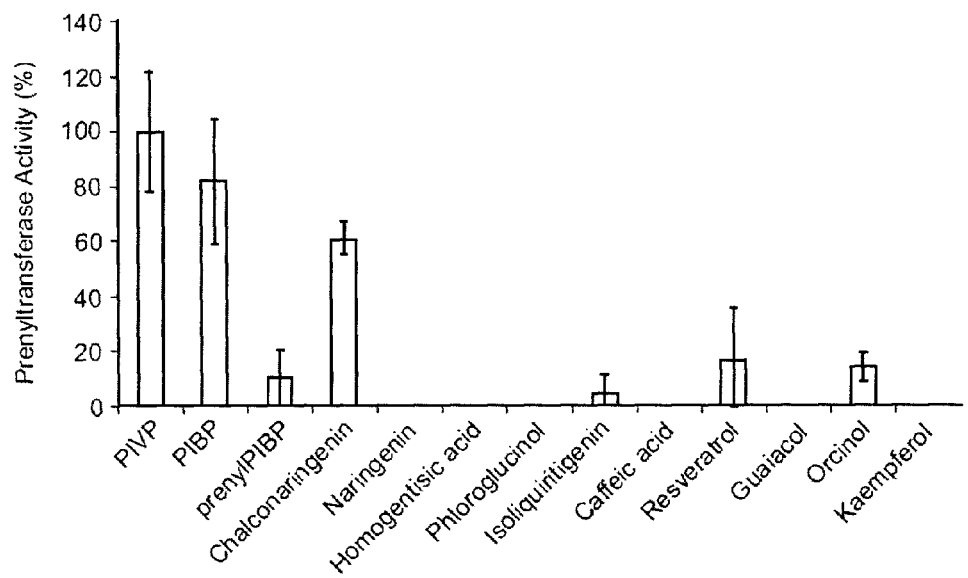
FIG. 9 depicts HIPT1 prenyltransferase activity with different acceptor (9A) and prenyl donor (9B) substrates.
Figure 9B:
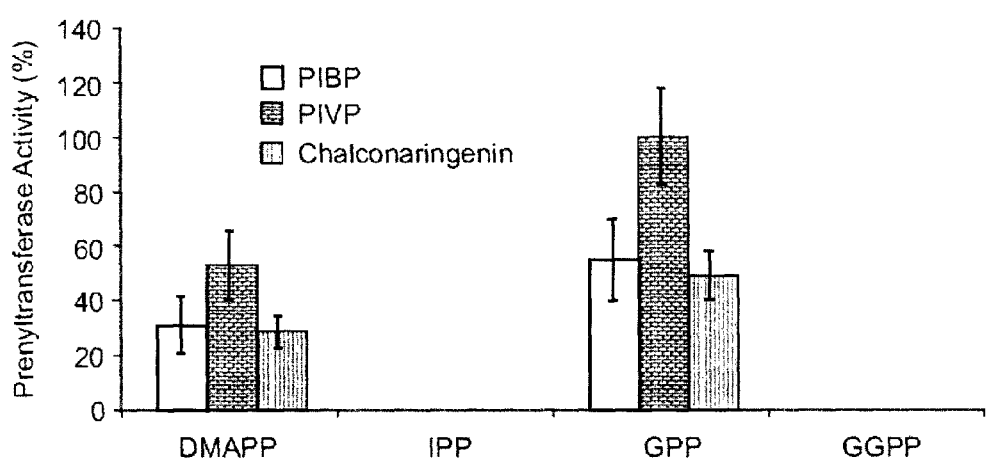

Referring to FIG. 9A, prenyltransferase activity of HIPT1 on various substrates was measured using $^{14}$C-DMAPP and thirteen aromatic acceptor substrates. Prenylated products were detected and quantified using radioHPLC. Error bars are SD (n=3). Referring to FIG. 9B, prenyltransferase activity of HIPT1 was measured with different prenyl diphosphate donors and the three major aromatic acceptor substrates, PIBP, PIVP and chalconaringenin. Prenylated products were quantified using HPLC with UV detection. Abbreviations: PIBP, phlorisobutyrophenone, PIVP, phlorisovalerophenone; DMAPP, dimethylallyl diphosphate; IPP, isopentenyl diphosphate; GPP, geranyl diphosphate; GGPP, geranylgeranyl diphosphate. Error bars are SD (n=3).

While HIPT1 is fairly specific for PIVP, PIBP and chalconaringenin, it does show some interesting activities with other substrates. Further, HIPT1 does prenylate prenyl-PIBP to form diprenyl-PIBP and it can accept a few other phenolic substrates such as isoliquiritigenin, resveratrol and orcinol. HIPT1 also appears to be fairly non-specific in the prenyl groups it can transfer and even prefers to transfer geranyl (C10) groups more than the C5 groups from dimethylallyl diphosphate.

Example 5

Physical and Chemical Properties of HIPT1

Figure 10A:
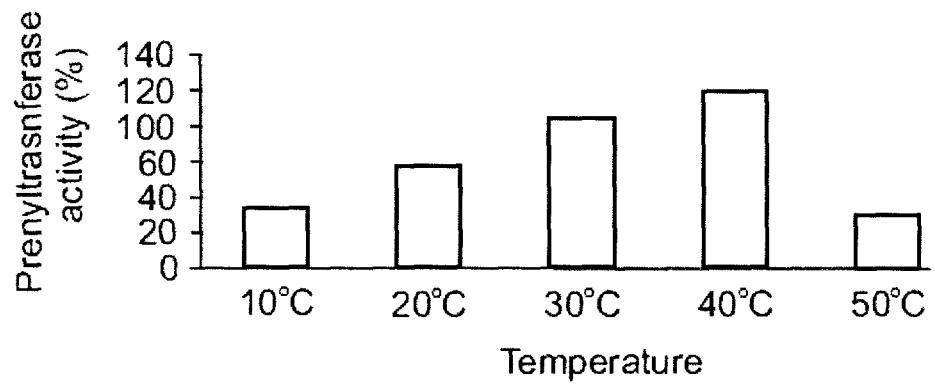
FIG. 10 depicts HIPT1 prenyltransferase activity at different temperatures (10A), with different divalent cations (10B) and at different pH (10C).
Figure 10B:
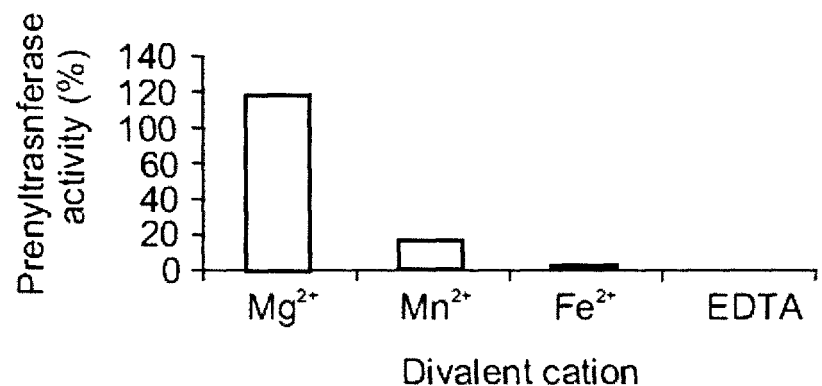
Figure 10C:
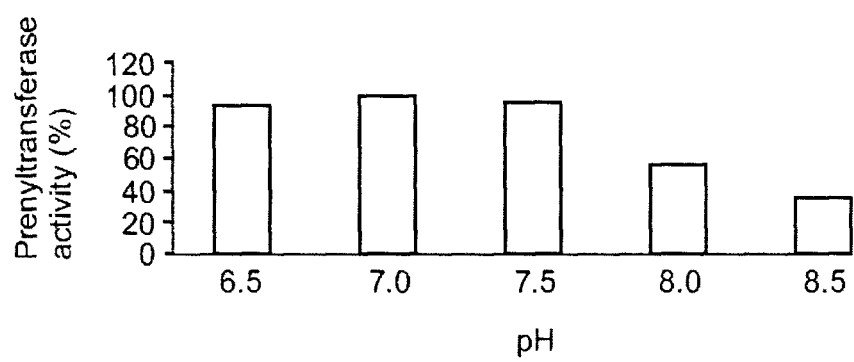

Referring to FIG. 10, the HIPT1 enzyme showed the highest activity at 40° C. in the presence of $Mg^{2+}$ as divalent cation. The presence of EDTA completely inhibited prenyltransferase activity, indicating that divalent cations are required for the function of HIPT1. The enzyme was active over the pH range 6.5 to 8.5, with the highest activity at pH 7.0.

Example 6

Expression of Terpenophenolic Enzymes in Hop Tissues

Figure 11:
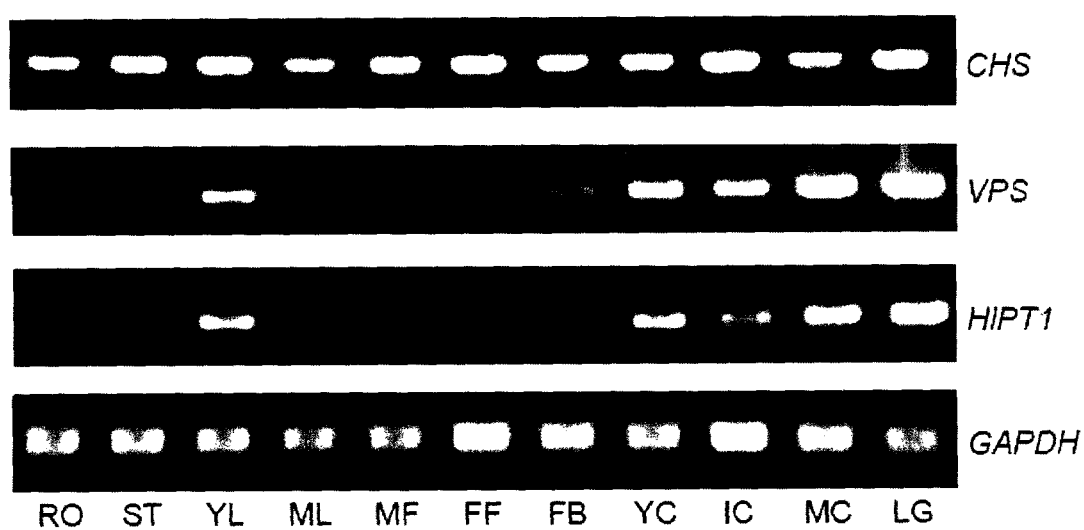
FIG. 11 depicts RT-PCR analysis of gene expression in hop organs and tissues.

With reference to FIG. 11, RNA isolated from different organs and tissues (RO, root; ST, stem; YL, young leaf; ML, mature leaf; MF, male flower; FF, female flower; FB, flower bud; YC, young cone; IC, intermediate cone; MC, mature cone; LG, lupulin gland) was reversed transcribed into cDNA. Gene-specific primers were used to amplify the transcripts encoding the biosynthetic enzymes CHS (chalcone synthase), VPS (valerophenone synthase) and HIPT1 (aromatic prenyltransferase). The housekeeping enzyme GAPDH (glyceraldehye 3-phosphate dehydrogenase) was used to ensure equal amplification in all samples. The HIPT1 gene is expressed in young leaves and at increasing levels as hop cones mature. HIPT1 transcripts are found at its highest levels in hop lupulin glands. This expression pattern is similar to that of VPS, which is the first enzyme in bitter acid biosynthesis, but unlike that of CHS, which is expressed in all organs and tissues.

References: The contents of the entirety of each of which are incorporated by this reference.

Alvarez J P, Pekker I, Goldshmidt A, Blum E, Amsellem Z, Eshed Y (2006) Endogenous and synthetic microRNAs stimulate simultaneous, efficient, and localized regulation of multiple targets in diverse species. *Plant Cell* 18:1134-51.

Bechtold N, Ellis J, Pelletier G (1993) In planta *Agrobacterium*-mediated gene transfer by infiltration of adult *Arabidopsis thaliana* plants. *C R Acad Sci Paris, Sciences de la vie/Life sciences* 316: 1194-1199.

Becker D, Brettschneider R, Lorz H (1994) Fertile transgenic wheat from microprojectile bombardment of scutellar tissue. *Plant J.* 5: 299-307.

Colgate E C, Miranda C L, Stevens J F, Bray T M, Ho E (2006) Xanthohumol, a prenylflavonoid derived from hops induces apoptosis and inhibits NF-kappaB activation in prostate epithelial cells. *Cancer Lett* 246: 201-209.

Collakova E, DellaPenna D (2001) Isolation and functional analysis of homogentisate phytyltransferase from *Synechocystis* sp. PCC 6803 and Arabidopsis. *Plant Physiol* 127: 1113-1124.

Datla R, Anderson J W, Selvaraj G (1997) Plant promoters for transgene expression. *Biotechnology Annual Review* 3: 269-296.

DeBlock M, DeBrouwer D, Tenning P (1989) Transformation of *Brassica napus* and *Brassica oleracea* using *Agrobacterium tumefaciens* and the expression of the bar and neo genes in the transgenic plants. *Plant Physiol.* 91: 694-701.

Depicker A, Montagu M V (1997) Post-transcriptional gene silencing in plants. *Curr Opin Cell Biol* 9:373-82.

Fung S Y, Zuurbier K W M, Paniego N B, Scheffer J J C, Verpoorte R (1997) Conversion of deoxyhumulone into the hop [alpha]-acid humulone, *Phytochemistry* 44: 1047-1053.

Goto K, Asai T, Hara S, Namatame I, Tomoda H, Ikemoto M, Oku N (2005) Enhanced antitumor activity of xanthohumol, a diacylglycerol acyltransferase inhibitor, under hypoxia. *Cancer Lett* 219: 215-222.

Helliwell C A, Waterhouse P M (2005) Constructs and methods for hairpin RNA-mediated gene silencing in plants. *Methods Enzymology* 392:24-35.

Henikoff S, Till B J, Comai L (2004) TILLING. Traditional mutagenesis meets functional genomics. *Plant Physiol* 135:630-6.

Jennewein S, Long R M, Williams R M, Croteau R (2004) Cytochrome p450 taxadiene 5alpha-hydroxylase, a mechanistically unusual monooxygenase catalyzing the first oxygenation step of taxol biosynthesis. *Chem Biol* 11: 379-387.

Katavic V, Haughn G W, Reed D, Martin M, Kunst L (1994) In planta transformation of *Arabidopsis thaliana*. *Mol. Gen. Genet.* 245: 363-370.

Katsuyama Y, Funa N, Miyahisa I, Horinouchi S (2007) Synthesis of unnatural flavonoids and stilbenes by exploiting the plant biosynthetic pathway in *Escherichia coli*. *Chem. Biol.* 14(6): 613-21.

Lamy V, Roussi S, Chaabi M, Gosse F, Schall N, Lobstein A, Raul F (2007) Chemopreventive effects of lupulone, a hop {beta}-acid, on human colon cancer-derived metastatic SW620 cells and in a rat model of colon carcinogenesis. *Carcinogenesis* 28: 1575-1581.

Lee J C, Kundu J K, Hwang D M, Na H K, Surh Y J (2007) Humulone inhibits phorbol ester-induced COX-2 expression in mouse skin by blocking activation of NF-kappaB and AP-1: IkappaB kinase and c-Jun-N-terminal kinase as respective potential upstream targets. *Carcinogenesis* 28: 1491-1498.

Leonard E, Yan Y, Fowler Z L, Li Z, Lim C G, Lim K H, Koffas M A (12 Mar. 2008) Strain Improvement of Recombinant *Escherichia coli* for Efficient Production of Plant Flavonoids. *Mol. Pharm.* [Epub ahead of print] PMID: 18333619 [PubMed—as supplied by publisher].

Matousek J, Novak P, Briza J, Patzak J, Niedermeierova H (2002) Cloning and characterisation of chs-specific DNA and cDNA sequences from hop (*Humulus lupulus* L.). *Plant Science* 162: 1007-1018.

Meyer P (1995) Understanding and controlling transgene expression. *Trends in Biotechnology*, 13: 332-337.

Milligan S R, Kalita J C, Pocock V, Van De Kauter V, Stevens J F, Deinzer M L, Rong H, De Keukeleire D (2000) The endocrine activities of 8-prenylnaringenin and related hop (*Humulus lupulus* L.) flavonoids. *Journal of Clinical Endocrinology and Metabolism* 85: 4912-4915.

Moloney M M, Walker J M, Sharma K K (1989) High efficiency transformation of *Brassica napus* using *Agrobacterium* vectors. *Plant Cell Rep.* 8: 238-242.

Nagel J, Culley L K, Lu Y, Liu E, Matthews P D, Stevens J F, Page J E (2008) EST analysis of hop glandular trichomes identifies an O-methyltransferase that catalyzes the biosynthesis of xanthohumol. *Plant Cell* 20: 186-200.

Nehra N S, Chibbar R N, Leung N, Caswell K, Mallard C, Steinhauer L, Baga M, Kartha K K (1994) Self-fertile transgenic wheat plants regenerated from isolated scutellar tissues following microprojectile bombardment with two distinct gene constructs. *Plant J.* 5: 285-297.

Okada Y, Ito K (26 Aug. 1999) Isolated and Purified Nucleic Acids Comprising a Gene Specifically Expressed in Hop Glands. International Patent Publication WO 99/42599.

Okada Y, Ito K (18 Apr. 2002) Farnesyl Pyrophosphate Synthase Protein, Nucleic Acid and Promoter Region Thereof. International Patent Publication WO 02/31164.

Okada Y, Kaneko T (7 Nov. 2002) Novel Chalcone Synthase-Like Genes and Proteins. International Patent Publication WO 02/088350.

Page J E, Nagel J (2006) Biosynthesis of terpenophenolics in hop and *cannabis*. In JT Romeo, ed, *Integrative Plant Biochemistry*, Vol 40. Elsevier, Oxford, pp 179-210.

Paniego N B, Zuurbier K W, Fung S Y, van der Heijden R, Scheffer J J, Verpoorte R (1999) Phlorisovalerophenone synthase, a novel polyketide synthase from hop (*Humulus lupulus* L.) cones. *European Journal of Biochemistry* 262: 612-616.

Potrykus I (1991) Gene transfer to plants: Assessment of published approaches and results. Annu. Rev. Plant Physiol. *Plant Mol. Biol.* 42: 205-225.

Pouwels et al., *Cloning Vectors. A Laboratory Manual*, Elsevier, Amsterdam (1986).

Ralston L, Subramanian S, Matsuno M, Yu O (2005) Partial reconstruction of flavonoid and isoflavonoid biosynthesis in yeast using soybean type I and type II chalcone isomerases. *Plant Physiol.* 137(4): 1375-88.

Rhodes C A, Pierce D A, Mettler I J, Mascarenhas D, Detmer J J (1988) Genetically transformed maize plants from protoplasts. *Science* 240: 204-207.

Sambrook et al, *Molecular Cloning: A Laboratory Manual,* *Third Edition,* Cold Spring Harbor, N.Y. (2001).

Sanford J C, Klein T M, Wolf E D, Allen N (1987) Delivery of substances into cells and tissues using a particle bombardment process. *J. Part. Sci. Technol.* 5: 27-37.

Sasaki K, Mito K, Ohara K, Yamamoto H, Yazaki K (2008) Cloning and characterization of naringenin 8-prenyltransferase, a flavonoid-specific prenyltransferase of *Sophora flavescens. Plant Physiol* 146: 1075-1084.

Schwab R, Ossowski S, Riester M, Warthmann N, Weigel D (2006) Highly specific gene silencing by artificial microRNAs in *Arabidopsis. Plant Cell* 18:1121-33.

Shimamoto K, Terada R, Izawa T, Fujimoto H (1989) Fertile transgenic rice plants regenerated from transformed protoplasts. *Nature* 338: 274-276.

Shimamura M, Hazato T, Ashino H, Yamamoto Y, Iwasaki E, To be H, Yamamoto K, Yamamoto S (2001) Inhibition of angiogenesis by humulone, a bitter acid from beer hop. *Biochem Biophys Res Commun* 289: 220-224.

Siragusa G R, Haas G J, Matthews P D, Smith R J, Buhr R J, Dale N M, Wise M G (2008) Antimicrobial activity of lupulone against *Clostridium perfringens* in the chicken intestinal tract jejunum and caecum. *J Antimicrob Chemother* PMID: 18276602 2008 Feb. 18 [Epub ahead of print].

Songstad D D, Somers D A, Griesbach R J (1995) Advances in alternative DNA delivery techniques. *Plant Cell, Tissue and Organ Culture* 40:1-15.

Stam M, de Bruin R, van Blokland R, van der Hoorn R A, Mol J N, Kooter J M (2000) Distinct features of post-transcriptional gene silencing by antisense transgenes in single copy and inverted T-DNA repeat loci. *Plant J.* 21:27-42.

Stevens J F, Page J E (2004) Xanthohumol and related prenylflavonoids from hops and beer: to your good health! *Phytochemistry* 65: 1317-1330.

Vasil I K (1994) Molecular improvement of cereals. *Plant Mol. Biol.* 25: 925-937.

Verzele M (1986) Centenary review: 100 Years of hop chemistry and its relevance to brewing. *J. Inst. Brew.* 92: 32-48.

Walden R, Wingender R (1995) Gene-transfer and plant regeneration techniques. *Trends in Biotechnology* 13: 324-331.

Wätjen W, Weber N, Lou Y J, Wang Z Q, Chovolou Y, Kampkötter A, Kahl R, Proksch P (2007) Prenylation enhances cytotoxicity of apigenin and liquiritigenin in rat H4IIE hepatoma and C6 glioma cells. *Food Chem. Toxicol.* 45(1): 119-24.

Yajima H, Ikeshima E, Shiraki M, Kanaya T, Fujiwara D, Odai H, Tsuboyama-Kasaoka N, Ezaki O, Oikawa S, Kondo K (2004) Isohumulones, bitter acids derived from hops, activate both peroxisome proliferator-activated receptor alpha and gamma and reduce insulin resistance. *J Biol Chem* 279: 33456-33462.

Yazaki K, Kunihisa M, Fujisaki T, Sato F (2002) Geranyl diphosphate: 4-hydroxybenzoate geranyltransferase from *Lithospermum erythrorhizon*. Cloning and characterization of a key enzyme in shikonin biosynthesis. *J Biol Chem* 277: 6240-6246.

Zanoli P, Zavatti M (2008) Pharmacognostic and pharmacological profile of *Humulus lupulus* L. *J Ethnopharmacol* 008 Jan. 20 [Epub ahead of print].

Zhang H, Wang Y, Pfeifer B A (31 Jan. 2008) Bacterial hosts for natural product production. *Mol. Pharm.* [Epub ahead of print] PMID: 18232637 [PubMed—as supplied by publisher].

Zuurbier K W M, Fung S Y, Scheffer J J, Verpoorte R (1998) In vitro prenylation of aromatic intermediates in the biosynthesis of bitter acids in *Humulus lupulus. Phytochemistry* 49: 2315-2322.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. An isolated or purified nucleic acid molecule comprising the nucleotide sequence as set forth in SEQ ID NO: 1 or 5.

2. An isolated or purified polypeptide comprising the amino acid sequence as set forth in SEQ ID NO: 2 or 6.

3. The polypeptide of claim 2 having aromatic prenyltransferase activity.

4. A vector, construct or expression system comprising the nucleic acid molecule as defined in claim 1.

5. A method of decreasing levels of terpenophenolic compounds in an organism, cell or tissue comprising transgenically expressing a nucleic acid molecule as defined in claim 1, or a part thereof, to silence an aromatic prenyltransferase gene in the organism, cell or tissue, in comparison to the same organism, cell or tissue grown under the same conditions but without the use of the nucleic acid molecule for silencing.

6. A method of increasing levels of terpenophenolic compounds in an organism, cell or tissue comprising transgenically expressing or over-expressing a nucleic acid molecule as defined in claim 1 in the organism, cell or tissue, in comparison to the same organism, cell or tissue grown under the same conditions but without the expressing or over-expressing of the nucleic acid molecule.

7. A method of increasing levels of terpenophenolic compounds in an organism, cell or tissue comprising transgenically expressing or over-expressing a nucleic acid molecule encoding a polypeptide as defined in claim 3 in the organism, cell or tissue, in comparison to the same organism, cell or tissue grown under the same conditions but without the expressing or over-expressing of the nucleic acid molecule.

8. The method of claim 6, wherein the organism is a microorganism.

9. The method of claim 8, wherein the microorganism is yeast or *E. coli*.

10. The method of claim 6, wherein the level of the terpenophenolic compound is increased.

11. The method of claim 6, wherein the nucleic acid molecule is transgenically expressed or over-expressed in combination with expression or overexpression of one or more other nucleic acids that encode one or more enzymes in a terpenophenolic biosynthetic pathway.

12. The method of claim 11, wherein the one or more enzymes in a terpenophenolic biosynthetic pathway is one or more of a valerophenone synthase, a chalcone synthase, a deoxyhumulone oxidase, or a desmethylxanthohumol O-methyltransferase.

* * * * *

SEQUENCE LISTING

```
<160> NUMBER OF SEQ ID NOS: 6

<210> SEQ ID NO 1
<211> LENGTH: 1239
<212> TYPE: DNA
<213> ORGANISM: Humulus lupulus

<400> SEQUENCE: 1
atggagctct cttcagtttc tagcttttca cttggaacta atccatttat atcaatcccc      60
cataataata ataatctcaa ggtctcatct tactgttgta aaagcaagag cagagtaatc     120
aattccacaa actcaaagca ttgttccccc aacaacaaca gcaacaacaa cacctctaac     180
aagacaacac atcttcttgg gttgtacgga cagagcagat gcttattaaa acctttatca     240
tttatcagct gcaacgacca aagggaaat tcaattaggg cttctgcaca aattgaagat     300
cgacctcctg aatctggaaa tctttcggca cttacaaatg ttaaagactt tgtaagtgta     360
tgttgggagt atgtaagacc atacacagca aaaggagtta ttatatgctc tagttgttta     420
tttggaagag aattgttgga gaacccaaat ctatttagtt ggcctctaat ttttagggca     480
ctcttgggaa tgttggctat actgggctct tgttttttata cagctggcat caatcaaatt     540
tttgatatgg atattgacag gataaacaaa ccagatttac cactggtttc agggcgtatt     600
```

```
tctgtggaat cagcttggtt attgacgtta agtcctgcaa taattggctt catattgatt    660
cttaaattga actcaggacc actccttact tctctatact gtttggccat tttgagtggg    720
actatctatt ctgttcctcc atttagatgg aagaagaatc ccattacagc atttctttgt    780
attcttatga ttcatgcagg tttaaacttt tctgtatatt atgcctctag agcagcactt    840
ggacttgcat ttgcatggag cccttcattt tccttcatca ctgcctttat tacatttatg    900
acgctaacgt tggcttcctc caaagatctt tctgacataa atggagatcg caagtttggt    960
gttgaaacct ttgcaaccaa gcttggtgca aaaaacatta cattacttgg cacaggactt   1020
ctcctcctaa actatgtagc agctatatct actgccatta tatggcctaa ggctttcaag   1080
agtaacataa tgctgctttc tcatgcaatc ttagcatttt ccttaatctt ccaggctcga   1140
gagttggatc gaacgaacta cactccggaa gcgtgcaaaa gcttctatga attcatctgg   1200
atcctcttct ctgcggaata cgttgtatat ctgttcatt                          1239
```

<210> SEQ ID NO 2
<211> LENGTH: 413
<212> TYPE: PRT
<213> ORGANISM: Humulus lupulus

<400> SEQUENCE: 2

```
Met Glu Leu Ser Ser Val Ser Ser Phe Ser Leu Gly Thr Asn Pro Phe
1               5                   10                  15

Ile Ser Ile Pro His Asn Asn Asn Asn Leu Lys Val Ser Ser Tyr Cys
            20                  25                  30

Cys Lys Ser Lys Ser Arg Val Ile Asn Ser Thr Asn Ser Lys His Cys
        35                  40                  45

Ser Pro Asn Asn Asn Ser Asn Asn Asn Thr Ser Asn Lys Thr Thr His
    50                  55                  60

Leu Leu Gly Leu Tyr Gly Gln Ser Arg Cys Leu Leu Lys Pro Leu Ser
65                  70                  75                  80

Phe Ile Ser Cys Asn Asp Gln Arg Gly Asn Ser Ile Arg Ala Ser Ala
                85                  90                  95

Gln Ile Glu Asp Arg Pro Pro Glu Ser Gly Asn Leu Ser Ala Leu Thr
            100                 105                 110

Asn Val Lys Asp Phe Val Ser Val Cys Trp Glu Tyr Val Arg Pro Tyr
        115                 120                 125

Thr Ala Lys Gly Val Ile Ile Cys Ser Ser Cys Leu Phe Gly Arg Glu
    130                 135                 140

Leu Leu Glu Asn Pro Asn Leu Phe Ser Trp Pro Leu Ile Phe Arg Ala
145                 150                 155                 160

Leu Leu Gly Met Leu Ala Ile Leu Gly Ser Cys Phe Tyr Thr Ala Gly
                165                 170                 175

Ile Asn Gln Ile Phe Asp Met Asp Ile Asp Arg Ile Asn Lys Pro Asp
            180                 185                 190

Leu Pro Leu Val Ser Gly Arg Ile Ser Val Glu Ser Ala Trp Leu Leu
        195                 200                 205

Thr Leu Ser Pro Ala Ile Ile Gly Phe Ile Leu Ile Leu Lys Leu Asn
    210                 215                 220

Ser Gly Pro Leu Leu Thr Ser Leu Tyr Cys Leu Ala Ile Leu Ser Gly
225                 230                 235                 240

Thr Ile Tyr Ser Val Pro Pro Phe Arg Trp Lys Lys Asn Pro Ile Thr
                245                 250                 255

Ala Phe Leu Cys Ile Leu Met Ile His Ala Gly Leu Asn Phe Ser Val
            260                 265                 270
```

```
Tyr Tyr Ala Ser Arg Ala Ala Leu Gly Leu Ala Phe Ala Trp Ser Pro
            275                 280                 285

Ser Phe Ser Phe Ile Thr Ala Phe Ile Thr Phe Met Thr Leu Thr Leu
        290                 295                 300

Ala Ser Ser Lys Asp Leu Ser Asp Ile Asn Gly Asp Arg Lys Phe Gly
305                 310                 315                 320

Val Glu Thr Phe Ala Thr Lys Leu Gly Ala Lys Asn Ile Thr Leu Leu
                325                 330                 335

Gly Thr Gly Leu Leu Leu Leu Asn Tyr Val Ala Ala Ile Ser Thr Ala
            340                 345                 350

Ile Ile Trp Pro Lys Ala Phe Lys Ser Asn Ile Met Leu Leu Ser His
        355                 360                 365

Ala Ile Leu Ala Phe Ser Leu Ile Phe Gln Ala Arg Glu Leu Asp Arg
    370                 375                 380

Thr Asn Tyr Thr Pro Glu Ala Cys Lys Ser Phe Tyr Glu Phe Ile Trp
385                 390                 395                 400

Ile Leu Phe Ser Ala Glu Tyr Val Val Tyr Leu Phe Ile
                405                 410
```

```
<210> SEQ ID NO 3
<211> LENGTH: 34
<212> TYPE: DNA
<213> ORGANISM: Artificial
<220> FEATURE:
<223> OTHER INFORMATION: Primer

<400> SEQUENCE: 3
cctagtcgac atggagctct cttcagtttc tagc                              34

<210> SEQ ID NO 4
<211> LENGTH: 34
<212> TYPE: DNA
<213> ORGANISM: Artificial
<220> FEATURE:
<223> OTHER INFORMATION: Primer

<400> SEQUENCE: 4
taacgcggcc gcctaaatga acagatatac aacg                              34

<210> SEQ ID NO 5
<211> LENGTH: 1227
<212> TYPE: DNA
<213> ORGANISM: Humulus lupulus

<400> SEQUENCE: 5
atggagctct cttcagtttc tagcttttca cttggaacta atccatttat atcaatcccc    60
cataataata ataatctcaa ggtctcatct tactgttgta aaagcaagag cagagtaatc   120
aattccacaa actcaaagca ttgttccccc aacaacaaca cctctaacaa gacaacacat   180
cttcttgggt tgtacggaca gagcagatgc ttattaaaac ctttatcatt tatcagctgc   240
aacgaccaaa ggggaaattc aattagggct tctgcacaaa ttgaagatcg acctcctgaa   300
tctggaaatc tttcggcact tacaaatgtt aaagactttg taagtgtatg ttgggagtat   360
gtaagaccat acacagcaaa aggagttatt atatgctcta gttgtttatt ggaagagaa    420 ttgttggaga acccaaatct atttagttgg cctctaattt ttagggcact cttgggaatg   480
ttggctatac tgggctcttg tttttataca gctggcatca atcaaatttt tgatatggat   540
attgacagga taaacaaacc agatttacca ctggtttcag ggcgtatttc tgtggaatca   600
```

-continued

```
gcttggttat tgacgttaag tcctgcaata attggcttca tattgattct taaattgaac    660
tcaggaccac tccttacttc tctatactgt ttggccattt tgagtgggac tatctattct    720
gttcctccat ttagatggaa gaagaatccc attacagcat ttctttgtat cttatgatt    780 catgcaggtt taaactttc tgtatattat gcctctagag cagcacttgg acttgcattt     840
gcatggagcc cttcattttc cttcatcact gcctttatta catttatgac gctaacgttg    900
gcttcctcca aagatctttc tgacataaat ggagatcgca gtttggtgt tgaaaccttt     960 gcaaccaagc ttggtgcaaa aacattaca ttacttggca caggacttct cctcctaaac    1020
tatgtagcag ctatatctac tgccattata tggcctaagg ctttcaagag taacataatg    1080
ctgctttctc atgcaatctt agcattttcc ttaatcttcc aggctcgaga gttggatcga    1140
acgaactaca ctccggaagc gtgcaaaagc ttctatgaat tcatctggat cctcttctct    1200
gcggaatacg ttgtatatct gttcatt                                        1227
```

<210> SEQ ID NO 6
<211> LENGTH: 409
<212> TYPE: PRT
<213> ORGANISM: Humulus lupulus

<400> SEQUENCE: 6

```
Met Glu Leu Ser Ser Val Ser Ser Phe Ser Leu Gly Thr Asn Pro Phe
1               5                   10                  15

Ile Ser Ile Pro His Asn Asn Asn Leu Lys Val Ser Ser Tyr Cys
            20                  25                  30

Cys Lys Ser Lys Ser Arg Val Ile Asn Ser Thr Asn Ser Lys His Cys
        35                  40                  45

Ser Pro Asn Asn Asn Thr Ser Asn Lys Thr Thr His Leu Leu Gly Leu
    50                  55                  60

Tyr Gly Gln Ser Arg Cys Leu Leu Lys Pro Leu Ser Phe Ile Ser Cys
65                  70                  75                  80

Asn Asp Gln Arg Gly Asn Ser Ile Arg Ala Ser Ala Gln Ile Glu Asp
                85                  90                  95

Arg Pro Pro Glu Ser Gly Asn Leu Ser Ala Leu Thr Asn Val Lys Asp
            100                 105                 110

Phe Val Ser Val Cys Trp Glu Tyr Val Arg Pro Tyr Thr Ala Lys Gly
        115                 120                 125

Val Ile Ile Cys Ser Ser Cys Leu Phe Gly Arg Glu Leu Leu Glu Asn
    130                 135                 140

Pro Asn Leu Phe Ser Trp Pro Leu Ile Phe Arg Ala Leu Leu Gly Met
145                 150                 155                 160

Leu Ala Ile Leu Gly Ser Cys Phe Tyr Thr Ala Gly Ile Asn Gln Ile
                165                 170                 175

Phe Asp Met Asp Ile Asp Arg Ile Asn Lys Pro Asp Leu Pro Leu Val
            180                 185                 190

Ser Gly Arg Ile Ser Val Glu Ser Ala Trp Leu Leu Thr Leu Ser Pro
        195                 200                 205

Ala Ile Ile Gly Phe Ile Leu Ile Leu Lys Leu Asn Ser Gly Pro Leu
    210                 215                 220

Leu Thr Ser Leu Tyr Cys Leu Ala Ile Leu Ser Gly Thr Ile Tyr Ser
225                 230                 235                 240

Val Pro Pro Phe Arg Trp Lys Lys Asn Pro Ile Thr Ala Phe Leu Cys
                245                 250                 255

Ile Leu Met Ile His Ala Gly Leu Asn Phe Ser Val Tyr Tyr Ala Ser
            260                 265                 270
```

-continued

```
Arg Ala Ala Leu Gly Leu Ala Phe Ala Trp Ser Pro Ser Phe Ser Phe
        275             280             285

Ile Thr Ala Phe Ile Thr Phe Met Thr Leu Thr Leu Ala Ser Ser Lys
        290             295             300

Asp Leu Ser Asp Ile Asn Gly Asp Arg Lys Phe Gly Val Glu Thr Phe
305             310             315             320

Ala Thr Lys Leu Gly Ala Lys Asn Ile Thr Leu Leu Gly Thr Gly Leu
                325             330             335

Leu Leu Leu Asn Tyr Val Ala Ala Ile Ser Thr Ala Ile Ile Trp Pro
            340             345             350

Lys Ala Phe Lys Ser Asn Ile Met Leu Leu Ser His Ala Ile Leu Ala
        355             360             365

Phe Ser Leu Ile Phe Gln Ala Arg Glu Leu Asp Arg Thr Asn Tyr Thr
        370             375             380

Pro Glu Ala Cys Lys Ser Phe Tyr Glu Phe Ile Trp Ile Leu Phe Ser
385             390             395             400

Ala Glu Tyr Val Val Tyr Leu Phe Ile
                405
```